(12) United States Patent
Rana et al.

(10) Patent No.: US 10,639,274 B2
(45) Date of Patent: May 5, 2020

(54) LUBRICANT FORMULATION OF CARBAMOYLETHYL KATIRA AND A PROCESS FOR PREPARATION THEREOF

(71) Applicant: Council of Scientific & Industrial Research, New Delhi (IN)

(72) Inventors: Vikas Rana, Patiala (IN); Radhika Sharma, Patiala (IN); Sunil Kamboj, Patiala (IN); Kuldeep Singh, Patiala (IN); Sarasija Suresh, Bengaluru (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 0 days.

(21) Appl. No.: 15/751,115

(22) PCT Filed: Aug. 5, 2016

(86) PCT No.: PCT/IN2016/050262
§ 371 (c)(1),
(2) Date: Feb. 7, 2018

(87) PCT Pub. No.: WO2017/025983
PCT Pub. Date: Feb. 16, 2017

(65) Prior Publication Data
US 2018/0235873 A1 Aug. 23, 2018

(30) Foreign Application Priority Data
Aug. 7, 2015 (IN) .......................... 2423/DEL/2015

(51) Int. Cl.
*A61K 9/00* (2006.01)
*A61K 31/715* (2006.01)
*A61K 47/36* (2006.01)

(52) U.S. Cl.
CPC .......... *A61K 9/0048* (2013.01); *A61K 31/715* (2013.01); *A61K 47/36* (2013.01)

(58) Field of Classification Search
CPC ..... A61K 9/0048; A61K 31/715; A61K 47/36
USPC ........................................................... 514/54
See application file for complete search history.

(56) References Cited

U.S. PATENT DOCUMENTS 6,056,950 A * 5/2000 Saettone .............. A61K 9/0048
424/78.04
2005/0250681 A1 11/2005 Molina

OTHER PUBLICATIONS

Sharma et al. Carbamoylethylation of guar gum. Carbohydrate Polymers 58 (2004) 449-453. (Year: 2004).*
Sharma et al. Feasibility and characterization of gummy exudate of Cochlospermumreligiosum as pharmaceutical excipient. Industrial Crops and Products 50 (2013) 776-786. (Year: 2013).*
Spencer et al. A Review of Acrylamide Neurotoxicity Part I. Properties, Uses and Human Exposure. Canadian Journal of Neurological Sciences, 1:151, 1974, p. 143-150. (Year: 1974).*
Rana et al., "Modified gums: Approaches and applications in drug delivery", Carbohydrate Polymers 83 (2011) 1031-1047.

* cited by examiner

*Primary Examiner* — Yih-Horng Shiao
(74) *Attorney, Agent, or Firm* — Blank Rome LLP

(57) ABSTRACT

A lubricant formulation of carbamoylethyl katira and a microwave assisted process for the preparation of the lubricant formulation of carbamoylethyl katira. The lubricant formulation of carbamoylethyl katira having antibacterial activity useful for eye lubricant based formulations, treatment of dry eye disease syndrome, etc.

14 Claims, 9 Drawing Sheets

| Time (hrs) | Eye lubricant formulation codes | | Inference |
|---|---|---|---|
| | $E_2$ | $E_6$ | |
| 0 | | | -No corneal irritation<br>-No conjuntival irritation<br>-No iris lesions<br>-No mucosal discharge |
| 1 | | | -No corneal irritation<br>-No conjuntival irritation<br>-No iris lesions<br>-No mucosal discharge |
| 4 | | | -No corneal irritation<br>-No conjuntival irritation<br>-No iris lesions<br>-No mucosal discharge |
| 24 | | | -No corneal irritation<br>-No conjuntival irritation<br>-No iris lesions<br>-No mucosal discharge |
| 72 | | | -No corneal irritation<br>-No conjuntival irritation<br>-No iris lesions<br>-No mucosal discharge |
| Conclusion: - $E_2$ and $E_6$ Eye lubricant formulations are non irritant and safe for ocular use. | | | |

Fig 7

| Eye lubricant formulations | E₁ | E₂ | E₅ | E₆ | Refresh tears (RT) | Hypromellose (HP) |
|---|---|---|---|---|---|---|
| Changes in eye during study period | | | | | | |
| Day 0 | No mucosal discharge, No inflammation and no swelling of eye lids | No mucosal discharge, No inflammation and no swelling of eye lids | No mucosal discharge, No inflammation and no swelling of eye lids | No mucosal discharge, No inflammation and no swelling of eye lids | No mucosal discharge, No inflammation and no swelling of eye lids | No mucosal discharge, No inflammation and no swelling of eye lids |
| *Before any administration* | | | | | | |
| *Administration of 0.2% w/v Benzalkonium Chloride to induce dry eye disease (2 drops twice a day for two days)* | | | | | | |
| Day 3 | Mucosal discharge, Inflammation and Swelling of eye lids | Mucosal discharge, Inflammation and Swelling of eye lids | Mucosal discharge, Inflammation and Swelling of eye lids | Mucosal discharge, Inflammation and Swelling of eye lids | Mucosal discharge, Inflammation and Swelling of eye lids | Mucosal discharge, Inflammation and Swelling of eye lids |

LUBRICANT FORMULATION OF CARBAMOYLETHYL KATIRA AND A PROCESS FOR PREPARATION THEREOF

RELATED APPLICATIONS

This application is a national phase application of PCT/IN2016/050262, filed Aug. 5, 2016, which claims priority to Indian Application No. 2423/DEL/2015, filed Aug. 7, 2015. The entire contents of those applications are incorporated herein by reference.

FIELD OF THE INVENTION

The present invention relates to a lubricant formulation of carbamoylethyl katira. Particularly, the present invention relates to a process for the preparation of the lubricant formulation of carbamoylethyl katira. The present invention also relates to the microwave assisted process for the preparation of said formulation. More particularly, the present invention relates to the lubricant formulation of carbamoylethyl katira having antibacterial activity useful for eye lubricant based formulations, treatment of dry eye disease syndrome, etc.

BACKGROUND OF THE INVENTION

The prospect of natural gum is higher as synthetic polymers have certain disadvantages like high cost, toxicity, environmental pollution during synthesis, non-renewable and non-patient compliance etc. Hence, natural gums are widely used for conventional and novel dosage forms since these are chemically inert, non-toxic, biodegradable, non-expensive and easily available and these natural gums being modified in different ways to obtain better materials for drug delivery systems and thus can compare with available synthetic excipients. Various kinds of natural gums are used in food industry and are regarded as safe for human consumption. Gums have variety of applications in pharmacy (Prajapati, V. D., Jani, G. K., Moradiya, N. G., & Randeria, N. P. (2013). Pharmaceutical applications of various natural gums, mucilages and their modified forms. Carbohydrate polymers, 92(2), 1685-1699.). The natural gums have been studied for their application in different pharmaceutical dosage forms like matrix controlled system, film coating agents, buccal films, microspheres, nanoparticles, viscous liquid formulations like ophthalmic solutions, suspensions, implants and their applicability and efficacy has been proven. These have also been utilized as viscosity enhancers, stabilisers, disintegrants, solubilisers, emulsifiers, suspending agents, gelling agents and bioadhesives, binders in various dosage forms (Guo, J. H., Skinner, G. W., Harcum, W. W., & Barnum, P. E. (1998). Pharmaceutical applications of naturally occurring water-soluble polymers. Pharmaceutical science & technology today, 1(6), 254-261.). Exudates gums are polysaccharides produced by plants as a result of stress, including physical injury and fungal attack. Gum Arabic (*Acacia senegal*), gum Tragacanth (*Aatragalus gummifer*), gum Karaya (*Sterculia urens*), gum Ghatti (*Anogesissus latifolia*) and gum Katira (*C. religiosum*) have been used by humans for thousands of yeras in various food and pharmaceutical applications (Verbeken, D., Dierckx, S., & Dewettinck, K. (2003). Exudate gums: occurrence, production, and applications. Applied Microbiology and Biotechnology, 63(1), 10-21.). Natural gums have been modified to overcome certain drawbacks like uncontrolled rate of hydration, thickening, drop in viscosity on storage, solubility and microbial contamination. Various methods are available to modify the state of molecular interactions between polymers (Rana, V., Rai, P., Tiwary, A. K., Singh, R. S., Kennedy, J. F., & Knill, C. J. (2011). Modified gums: Approaches and applications in drug delivery. Carbohydrate Polymers, 83(3), 1031-1047.). Physical methods: molecular interactions between polymers can be achieved by exposure to heat, saturated steam, microwave technology and radiations. Chemical methods: polymers are treated with chemicals like aldehydes, epichlorohydrin, borex or gluteraldehyde.

Dry eye syndrome or dry eye (also known as *Keratoconjuctivitis sicca*) occurs when there is a problem with the tear film that normally keeps the eye moist and lubricated. It is evident from its name that *Keratoconjuctivitis sicca* is a drying inflammation: kerato (corneal) conjunctivitis (conjunctival inflammation) sicca (from the Latin sicco, meaning "to dry") (Vibhute, S., Kawtikwar, P., Kshirsagar, S., & Sakarkar, D. (2010). Formulation and evaluation of tear substitutes. International Journal of Pharmaceutical Sciences Review and Research, 2, 17-20.). It is a multi-factorial disease and is accompanied by increased osmolarity of the tear film and inflammation of ocular surface. Symptoms of dry eye vary among patients, and most commonly they include itching, grittiness, burning, and sensitivity to bright light, foreign-body sensation, irritation, pain, blurred vision, and contact lens intolerance. Dry eyes can affect anyone, but it becomes more common with increasing age (Brewitt, H., & Sistani, F. (2001). Dry eye disease: the scale of the problem. Survey of ophthalmology, 45, S199-S202.). A dry eye affects about 7% people in their 50 s, and about 15% people in their 70 s. Women are affected more often than men (Lee, A. J., Lee, J., Saw, S. M., Gazzard, G., Koh, D., Widjaja, D., & Tan, D. T. H. (2002). Prevalence and risk factors associated with dry eye symptoms: a population based study in Indonesia. British Journal of Ophthalmology, 86(12), 1347-1351.). The choice of therapy for dry eye disease may be determined by the severity of the condition. Mild cases of dry eye, in which there are no signs of damage to the conjunctiva or cornea, may be successfully managed with artificial tears applied up to four times per day. In moderate cases of dry eye, examination will reveal mild damage to the cornea, such as superficial punctate keratopathy (SPK) limited to certain zones. In these cases, more frequent treatment will be required, e.g., use of unpreserved artificial tears up to 12 times per day and an unpreserved lubricating ointment at bedtime. Severe dry eye can be characterized by keratinisation of the conjunctiva and moderate to severe corneal damage, including SPK, filaments, epithelial defects, and a subsequently higher risk of secondary infections. In addition to frequent instillation of unpreserved artificial tears and lubricating ointment at night, severe cases of dry eye will require other treatment strategies, such as tear-conserving therapies (Calonge, M. (2001). The treatment of dry eye. Survey of ophthalmology, 45, S227-S239.).

Katira gum is an exudate gum, polysaccharide produced by plants as a result of stress, including physical injury and fungal attack. The gum is secreted by *Cochlospermum religiosum* (A small or medium sized, deciduous, soft wooded tree). The katira gum used in the present invention was purchased from "Monu Di Hatti" Kiryana store, Badala Rode, Kharar, Bill No. 521, Dated: 7 Jan. 2013. Katira gum is pale and semi-transparent, insoluble in water, but swells into a pasty transparent mass with water. The gum is sweet, thermogenic, anodyne, sedative and effective in cough, dysentery, diarrohoea, gonorrhea, syphilis, trachoma and antilice.

The heteropolysaccharide isolated from the gum (Katira) was found to consist of D-galactose, D-galactrouronic acid and L-rhamnose in a molar ratio 2:1:3 (Ojha, A. K., Maiti, D., Chandra, K., Mondal, S., Roy, D. D. S. K., Ghosh, K., & Islam, S. S. (2008). Structural assignment of a heteropolysaccharide isolated from the gum of *Cochlospermum religiosum* (Katira gum). Carbohydrate research, 343(7), 1222-1231).

A polysaccharide grafted katira gum was synthesized by graft acrylamide on katira gum in presence of varying concentration of cerric ammonium nitrate (CAN) as initiator. This modified gum was found to be useful as an excipient for colon targeting of drugs (Bharaniraja, B., Jayaram Kumar, K., Prasad, C. M., & Sen, A. K. (2011). Modified katira gum for colon targeted drug delivery. Journal of Applied Polymer Science, 119(5), 2644-2651; Bharaniraja, B., Kumar, K. J., Prasad, C. M., & Sen, A. K. (2011). Different approaches of katira gum formulations for colon targeting. International journal of biological macromolecules, 49(3), 305-310). The synthesis of acrylamide grafted katira gum requires a heating step at 60° C. for maximum of 5 hr on a water bath. Thus, the method proposed in the invention is microwave assisted and requires 15-20 minutes to complete the reaction process. Hence, the process proposed is considered have high industrial acceptance. A green synthesis of gold nanoparticles using aqueous solution of a hetero-polysaccharide, extracted from the katira gum and found to be useful as a efficient heterogeneous catalyst in the reduction of 4-nitrophenol to 4-aminophenol (Maity, S., Sen, I. K., & Islam, S. S. (2012). Green synthesis of gold nanoparticles using gum polysaccharide of *Cochlospermum religiosum* (katira gum) and study of catalytic activity. Physica E: Low-dimensional Systems and Nanostructures, 45, 130-134). Therefore, the method involves catalytic reduction of gum katira employing direct heating at 70° C. for 6 hr to prepare gold nanoparticles. However, the present invention provides microwave assisted method and requires less time to complete the reaction. The katira gum has been successfully used as a gelling agent in tissue culture media for in vitro shoot formation and rooting in *Syzygium cuminii* and somaic embryogenesis in *Albizzia lebbeck* (Jain, N., & Babbar, S. B. (2002). Gum katira—a cheap gelling agent for plant tissue culture media. Plant cell, tissue and organ culture, 71(3), 223-229).

In a different investigation methanolic extracts of leaves and flowers of *Cochlospermum ereligiosum* linn. was found to show antibacterial activity against eight strains of bacterial species, viz., *Staphylococcus aureus, Salmonella typhi, Enterobacter aerogenes, Pseudomonas aeruginosa, Xanthomonas oryzae* pv. *oryzae, Xanthomonas axonopodis* pv. *malvacearum, Bacillus cereus* and *Micrococcus* sp. (Bai, J. A., Rai, R. V., & Samaga, P. V. (2011). Evaluation of the antimicrobial activity of three medicinal plants of South India. Malaysian Journal of Microbiology, 7(1), 14-18). *Cochlospermum religiosum* is commonly called as Butter cup tree, Yellow silk cotton tree, Golden silk cotton tree is native of India, Burma and Thailand. The flowers of this tree are used for temple offerings. The synonyms of this plant are Bombax *gossypium, Cochlospermum gossypium, Maximilianea gossypium*. *Cochlospermum religiosum* is a small or medium sized, deciduous, soft wooded tree. The tree yields a gum that exudes from the fibrous, deeply furrowed bark, which is known as Katira gum (Prajapathi, N. D., Purohit, S. S., Sharma, A. K., & Kumar, T. (2003). A Handbook of medicinal plants: A complete source book. Section II, Published by Agrobios (India), Jodhpur, 27). *Cochlospermum religiosum* (L.) is extensively used in Ayurvedic medicines and other uses. Every part of this plant is used medicinally. It is also used for its anti-inflammatory activity in Siddha Drug 'Kalnar Parpam'. Gum katira is used as a cheap gelling agent for plant tissue culture and has wide application in pharmaceutical and food industries. Katira gum is pale and semi-transparent, insoluble in water, but swells into a pasty transparent mass with water. This gum has assumed great importance in recent years and exported annually from India for use in the cigar paste and ice-cream industry (Ojha, A. K., Maiti, D., Chandra, K., Mondal, S., Roy, D. D. S. K., Ghosh, K., & Islam, S. S. (2008). Structural assignment of a heteropolysaccharide isolated from the gum of *Cochlospermum religiosum* (Katira gum). Carbohydrate research, 343(7), 1222-1231).

Carboxymethylation as well as carbamoylethylation of *Cassia* gum is reported to improve cold water solubility, improve viscosity and increase microbial resistance as compared to native gum (Sharma, B. R., Kumar, V., & Soni, P. L. (2003). Carbamoylethylation of *Cassia* tora gum. Carbohydrate polymers, 54(2), 143-147; Soni, P. L., & Sharma, P. (2000). *Cassia* tora gum as viscosifier and fluid loss control agent. Indian Patent Application, (680)). Therefore, Rai et al (Rai, P. R., Tiwary, A. K., & Rana, V. (2012). Superior disintegrating properties of calcium cross-linked *Cassia fistula* gum derivatives for fast dissolving tablets. Carbohydrate Polymers, 87(2), 1098-1104) attempted to incorporate calcium or sodium salts of carboxymethylated or carbamoylethylated *C. fistula* gum as superdisintegrant in the formulation development of FDTs. Thus, the present invention relates to the method of converting water insoluble, low spreadability and high swellable katira gum in to water soluble, high swellable, high spreadable carbamoylethyl katira.

Microwaves comprise electromagnetic radiation in the frequency range of 300 MHz to 300 GHz. On exposure to microwaves, the charged or polar particles tend to align themselves with electric field component of the microwaves which rapidly reverses its direction e.g. at the rate of 2.4×109/s at 2.45 GHz microwave frequency. As the polar or charged particles in a reaction medium fail to align themselves as fast as the direction of the electric field of microwaves changes, friction is created to heat the medium (Galema, S. A. (1997). Microwave chemistry. Chem. Soc. Rev., 26(3), 233-238). This heat generated could be utilized to provide activation energy for the reaction. In addition, in the microwave heating process, the high temperatures attained and the ability to work under high pressure conditions for relatively short times make reactions faster than under conventional thermal conditions, and limit the occurrence of slower side reactions. Thus, greater yields are usually obtained. (Kappe, C. O. (2004). Controlled microwave heating in modern organic synthesis. Angewandte Chemie International Edition, 43(46), 6250-6284). Hence, the present invention utilized alternative microwave assisted method to prepare carbamoylethyl katira from katira gum.

Dry eye treatment poses a substantial challenge to the clinician. The main objectives in treatment for patients with dry eye disease are to improve the patient's comfort and quality of life, and to return the ocular surface and tear film to the normal homeostatic state. Symptoms can rarely be eliminated, but they can often be improved. Eye lubricants are used to increase humidity at the ocular surface (Pinho Tavares, F. D., Fernandes, R. S., Bernardes, T. F., Bonfioli, A. A., & Carneiro Soares, E. J. (2010, May). Dry eye disease. In Seminars in ophthalmology (Vol. 25, No. 3, pp. 84-93). London, UK: Informa UK Ltd).

The extract obtained from leaves and flowers of *Cochlospermum religiosum* linn was found to contain alkaloids, steroids, glycosides, saponins, flavonoids, tannins and phenols. However, no reports have been available for any anti bacterial activity of gum katira. Overall, the present invention involves a process for the preparation of carbamoylethyl Katira eye lubricant solution employing microwave assistance. The technique includes use of microwave that provides reaction activation energy much faster than heating on a water bath. In addition, non uniform distribution of heating rate on water bath sometimes leads to breakage of α-(1-4) linkage present in the polysaccharides. Hence, the microwave assisted process for the synthesis of carbamoylethyl Katira eye lubricant solution is fast, safe and industrially acceptable.

OBJECTIVES OF THE INVENTION

The main objective of the present invention is to provide a lubricant formulation of carbamoylethyl katira.

The another objective of the present invention is to provide a process for the preparation of the lubricant formulation of carbamoylethyl katira.

Another objective of the present invention is to provide a microwave assisted process for the preparation of the lubricant formulation of carbamoylethyl katira.

Yet another object is to provide the lubricant formulation of carbamoylethyl katira effective for remedy of dry eye disease.

Yet another object is to provide the lubricant formulation of carbamoylethyl katira effective against dry eye disease as compared to Refreash tears (NaCMC 0.5% w/v) and Hyperomellose (HPMC 0.3% w/v) available in the market.

Another objective of the present invention relates to the lubricant formulation of carbamoylethyl katira having antibacterial activity useful for eye lubricant based formulations, treatment of dry eye disease syndrome, etc.

SUMMARY OF THE INVENTION

Accordingly, the present invention relates to a lubricant formulation of carbamoylethyl katira comprising katira gum in the range of 5% w/v to 10% w/v carbamoylethyl in the range of 5% w/v to 10% w/v and additives.

In an embodiment, said katira gum is obtained from *Cochlospermum religiosum*.

In an embodiment, said additives are selected from the group consisting of a surfactant, emulsifier, and combinations thereof, in a water based emulsion.

In a preferred embodiment, said formulation shows antibacterial activity against *Staphylococcus aureus*.

In another preferred embodiment, said formulation is for use in treatment of dry eye disease.

In still an embodiment, a process for the preparation of the lubricant formulation of carbamoylethyl katira wherein said process comprises of the following steps:

a) soaking gum katira in water for a time period of 14 to 20 hrs to obtain homogenized gel;

b) stirring the homogenized gel obtained in step (a) for 30 to 45 minutes followed by addition of 25 ml of 28% w/v to 44% w/v ice cold sodium hydroxide solution with stirring and additional stirring for 30 min after the addition of ice cold sodium hydroxide to obtain basic reaction mixture;

c) adding 11% w/v to 18% w/v of acrylamide to the basic reaction mixture obtained in step (b) with constant stirring for 1 hr to obtain reaction mixture;

d) irradiating the reaction mixture obtained in step (c) in a microwave reactor at 450 watt for a time period of 0.5 to 1 min followed by a cooling cycle for a time period of 1 to 2 min at a temperature of 4° C. to 10° C. in ice bath;

e) repeating the step (d) for 3 to 7 times followed by neutralization with dilute glacial acetic acid to obtain neutralized reaction mixture;

f) precipitating the neutralized reaction mixture obtained in step (e) with solvents followed by washing with precipitating solvent to obtain precipitate of carbamoylethyl katira;

g) filtering and drying the precipitates of carbamoylethyl katira obtained in step (f) to obtain carbamoylethyl katira;

h) dissolving 2.5% to 10% w/v of carbamoylethyl katira obtained in step (g) in luke warm sterile water for injection followed by filtration through a 0.22 μm filtration system to obtain lubricant formulation of carbamoylethyl katira;

i) sterilizing the lubricant formulation of carbamoylethyl katira obtained in step (h) at a temperature in the range of 121° C. to 118° C. for a time period of 20 to 40 minutes to get sterilized lubricant formulation.

In yet another embodiment, the ratio of glacial acetic acid and water is 1:1 for neutralization of reaction.

In still another preferred embodiment, drying of carbamoylethyl katira is carried out using lyophilization at a temperature in the range of −80° C. for a time period of 72 to 96 hr or oven drying at a temperature selecting in the range of 45 to 55° C. for a time period selected in the range of 3.5 to 4.5 days or 60° C. for a time period selected in the range of 1.5 to 2.5 days to obtain the formulation of carbamoylethyl katira.

In still yet another preferred embodiment, a process for the preparation of carbamoylethyl katira, a novel eye lubricant solution in pharmaceutical and nutraceutical in general and for the treatment of dry eye disease.

In yet another embodiment, carbamoylethyl katira is prepared from a pure katira gum obtained from *Cochlospermum religiosum*.

In still another embodiment, a carbamoylethyl katira eye lubricant solution is obtained by the process as mentioned.

In still another embodiment, a sterile solution where the sterile solution is useful as eye lubricant effective for the remedy of dry eye disease.

Yet another embodiment, a sterile solution has eye lubricant activity at a concentration more than 2.5% w/v.

Yet another embodiment, the formulation for ocular delivery is prepared having 2.5%-10% w/v carbamoylethyl katira eye lubricant solution.

BRIEF DESCRIPTION OF THE FIGURES

FIG. 7 is a table showing results of a Draize test.

Figure 8B:
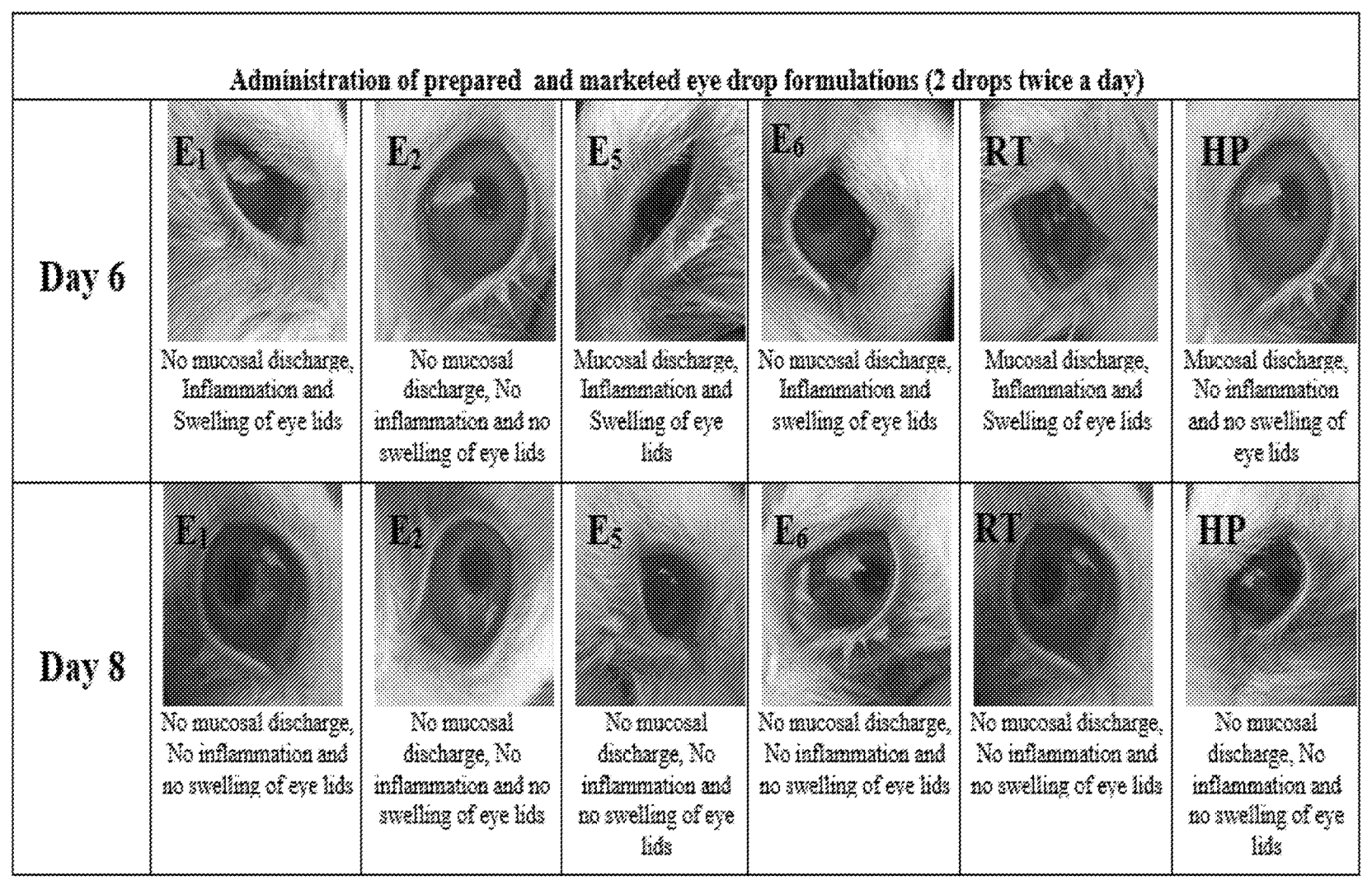

FIGS. 8A and 8B are tables showing results of a dry eye animal model.

DETAILED DESCRIPTION OF THE INVENTION

Figure 1:
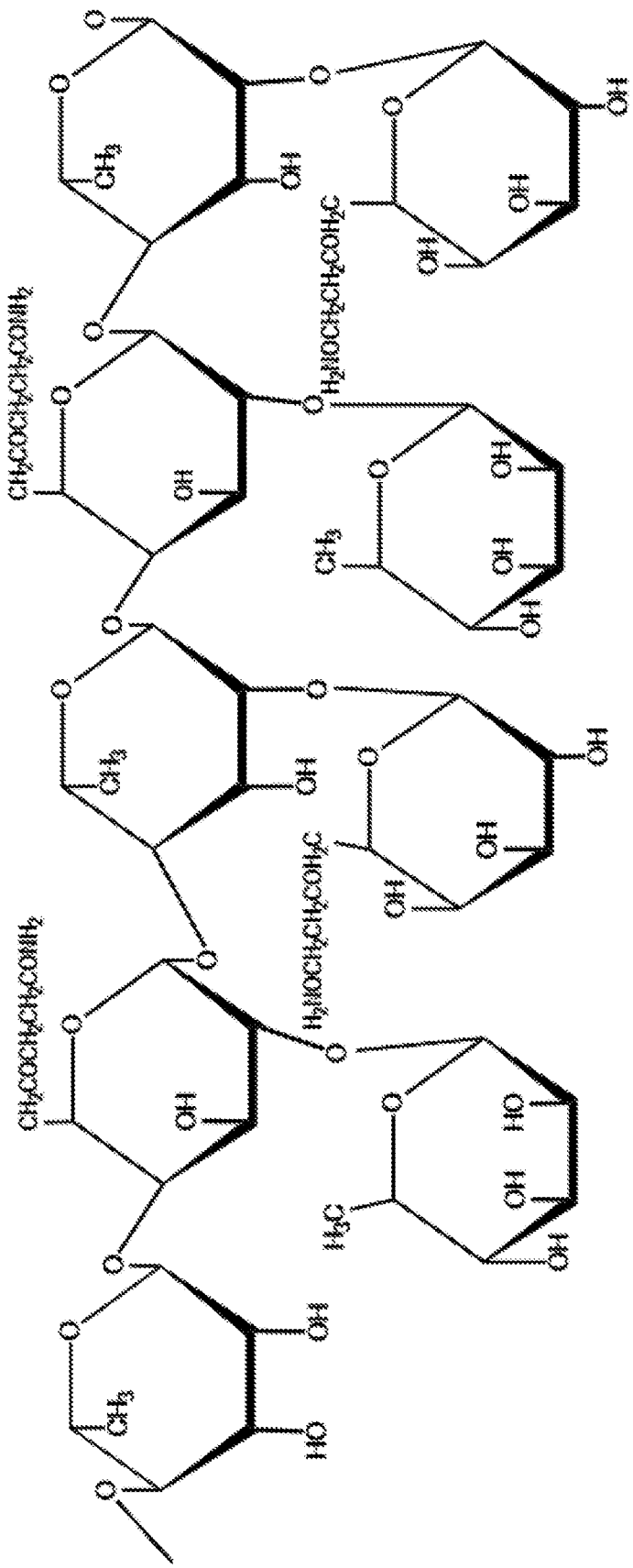
FIG. 1 Illustrates synthesis and advantage of carbamoylethyl katira gum

The present invention pertains to novel eye lubricant from a carbamoylethyl katira and its advantage as a potential antibacterial eye lubricant for dry eye disease. The initial step of the present invention relates to carbamoylethylation of katira gum, comprise katira gum, acrylamide (prop-2-enamide; $CH_2$=CH—$CONH_2$; as reactant), heating system as microwave operated at different conditions, precipitation stage is carried out with different solvents (acetone, methanol, ethanol, acetone:ethanol), drying phase in oven at different conditions (45° C. for 3.5 days, 60° C. for 2.5 days, 65° C. for 38 hrs or 70° C. for 28 hrs). The present invention pertain eye lubricant composition that treat dry eye disease.

The reaction parameters, which influence the carbamoylethylation process, are the solvent system, solvent composition, concentration of sodium hydroxide and concentration of acrylamide, reaction time and reaction temperature.

The carbamoylethylation was performed employing microwave technique, else conventional techniques which not provide carbamoylethylation of water insoluble katira gum.

The present invention includes reaction steps as:

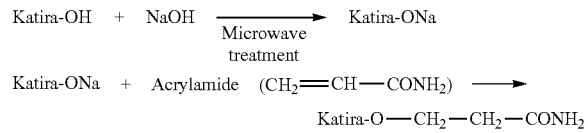

The present invention detailed the process of carbamoylethylation by varying the process parameters such as concentration of sodium hydroxide, concentration of acrylmide, microwave radiation, microwave radiation time, precipitating solvent system and drying phase. The effect of variation of sodium hydroxide concentration from microwave radiation (450 watt for 5 cycles, each cycle 0.5 min/cycle followed by 2 min cooling cycle) on degree of substitution was examined. The degree of substitution (DS) of the polymer is the average number of substitution group (—O—$CH_2$—$CH_2$—COONa) attached per base unit.

EXAMPLES

The following examples, which include preferred embodiments, will serve to illustrate the practice of this invention, it being understood that the particulars shown are by way of example and for purpose of illustrative discussion of preferred embodiments of the invention.

Table 1 Effect of concentration of sodium hydroxide on carbomoylethyl katira

Table 2 $3^2$ full factorial design for the synthesis of carbamoylethyl katira gum Table 3 Results of MALDI-TOF of carbamoylethyl katira gum Table 4 Results of rheological description evaluated using back extrusion Table 5 Results of Bacteriostatic activity of carbamoylethyl/carboxyethyl katira gum against *Staphylococcus aureus* using Serial dilution in liquid media method Table 6 Results of Bactericidal activity of carbamoylethyl/carboxyethyl katira gum against *Staphylococcus aureus* using End point or Extinction point method Table 7 Various eye lubricant formulations of carbamoylethyl/carboxyethyl katira gum Table 8 Physical properties of different eye lubricant solutions Table 9 Effect of concentration of eye lubricant solution on drop size Table 10 Effect of surface tension on drop size dispensed from a plastic dropper bottle Table 11 The effect on mean drop size of carbamoylethyl/carboxyethyl katira gum eye lubricant solution when dispensed at an angle 45° and 90°

Table 12 Results of In-vitro antimicrobial activity of eye lubricant solution

Table 13 Results of formulation stability study

Table 14 Results of Draize test

Table 15 Results of schirmer test for lacrimal secretion

Table 16 Results of dry eye animal model

Example-1: Screening of the Concentration of Alkali for Obtaining Maximum Yield of Carbamoylethyl Katira The gum katira (1 gm) was soaked in 100 mL of water until the gum completely swells. The homogenized gum solution was stirred for 30 min with the slow addition of 25 ml of 28% w/v, 36% w/v or 44% w/v ice cold sodium hydroxide solution (Table 1). Separately, 18% w/v (w.r.t total reaction mixture volume) acrylamide mixed with alkaline katira gum solution with constant stirring for 1 hr. The prepared mixture was microwaved (7 cycles, 450 W) for 0.5 min of hot cycle followed by 1 min cooling cycle. This solution was kept overnight to complete the reaction and by neutralization with dilute glacial acetic acid (1:1::glacial acetic acid:water). The neutralized reaction mixture was precipitated with acetone followed by washing with respective precipitating solvent. Filtered and dried the precipitates of carbamoylethyl katira using lyophilization at a temperature in the range of −80° C. for a time period of 72 to 96 hr. Thus 36% w/v concentration of sodium hydroxide was selected.

TABLE 1

Effect of concentration of sodium hydroxide on carboxymethyl katira

| Code | 25 ml volume of sodium hydroxide (% w/v) | % Nitrogen |
|---|---|---|
| PRL-1 | 28% | 1.88 |
| PRL-2 | 36% | 3.18 |
| PRL-3 | 44% | 2.58 |

*Keep all other parameters constant like 18% w/v (w.r.t total reaction mixture volume) acrylamide; microwave treatment: 7 cycles, 450 W, 0.5 min. hot cycle followed by 1 min. cold cycle.

Example-2

The gum katira (1 gm) was soaked in 100 mL water until the gum completely swells. The homogenized gum solution was stirred for 30 min with the slow addition of 25 ml of 36% w/v ice cold sodium hydroxide solution (Table 1). Separately, 18% w/v (w.r.t total reaction mixture volume) acrylamide mixed with alkaline katira gum solution with constant stirring for 1 hr. The prepared mixture was microwaved (3-7 cycles, 450 W) for 0.5 min/cycle followed by 1-2 min cooling cycle. This solution was kept overnight to complete the reaction and by neutralization with dilute glacial acetic acid (1:1::glacial acetic acid:water). The neutralized reaction mixture was precipitated with acetone followed by washing with respective precipitating solvent. Filtered and dried the precipitates of carbamoylethyl katira using lyophilization at a temperature in the range of −80° C. for a time period of 72 to 96 The process for the synthesis of carboxymethyl katira was conducted as per two factor three level ($3^2$) full factorial design (Gohel, M., Patel, M., Amin, A., Agrawal, R., Dave, R., & Bariya, N. (2004). Formulation design and optimization of mouth dissolve tablets of nimesulide using vacuum drying technique. AAPs PharmSciTech, 5(3), 10-15). The $X_1$ was amount of acrylamide added and $X_2$ was number of cycles. During preliminary studies, it was observed that the optimum concentration of sodium hydroxide i.e. 25 ml of 36% w/v is required to complete the reaction. After this concentration of sodium hydroxide, % nitrogen content decreases. Therefore, the composition of sodium hydroxide was fixed to 25 ml of 36% w/v. The amount acrylamide and number of heating cycles during microwave treatment was found to show significant effect on the degree of substitution (in terms of % nitrogen content) and % yield of carbamoylethyl katira.

Thus, both the factors were taken to optimize the synthesis of carbamoylethyl katira. The results were shown in the Table 2. The equation generated after multiple linear regression are:

$Y_1=0.26+0.053X_1+0.026X_2$; ($R^2=0.9317$)

$Y_2=92.21+2.78X_1+1.00X_2+0.25X_1X_2+0.53X_1^2+0.38X_2^2$; ($R^2=0.9824$)

The equations showed direct correlation of $Y_1$ (degree of substitution) and $Y_2$ (yield) on $X_1$ and $X_2$. Further, the increase in amount of monomer ($X_1$) and no. of cycles during microwave treatment ($X_2$) increased the yield and degree of substitution. The maximum yield and degree of substitution was found to obtain at 18% w/v (w.r.t total reaction mixture volume) of monomer and 7 cycles of microwave treatment (450 W, 0.5 min/cycle). i.e synthesis $S_9$. Therefore, further carbamoylethyl katira was synthesized with method of $S_9$ to get 97.5% yield.

TABLE 2

$3^2$ Full factorial design for the synthesis of carbamoylethyl katira

| | Independent variables | | Dependent variables | |
|---|---|---|---|---|
| Batch No. | $X_1$ (Conc. Monomer % w/v) | $X_2$ (no. of heating cycles) | $Y_1$ (Degree of substitution) | $Y_2$ (% yield) |
| S1 | −1 (11) | −1 (3) | 0.165 | 89.2 |
| S2 | −1 (11) | 0 (5) | 0.225 | 90.5 |
| S3 | −1 (11) | 1 (7) | 0.247 | 90.9 |
| S4 | 0 (14.5) | −1 (3) | 0.236 | 91.8 |
| S5 | 0 (14.5) | 0 (5) | 0.253 | 92.2 |
| S6 | 0 (14.5) | 1 (7) | 0.276 | 93.4 |
| S7 | 1 (18) | −1 (3) | 0.307 | 94.8 |
| S8 | 1 (18) | 0 (5) | 0.308 | 95.0 |
| S9 | 1 (18) | 1 (7) | 0.342 | 97.5 |
| $R^2$ | | | 0.9317 | 0.9824 |
| CV % | | | 4.80 | 0.40 |

| Variance analysis coefficients with magnitude | | | | | |
|---|---|---|---|---|---|
| Response | Intercept | $X_1$ | $X_2$ | $X_1 X_2$ | $X_1^2$ | $X_2^2$ |
| $Y_1$ | 0.26 | 0.053 | 0.026 | — | — | — |
| $Y_2$ | 92.21 | 2.78 | 1.00 | 0.25 | 0.53 | 0.38 |

| Numerical optimization | | | |
|---|---|---|---|
| Response | $Y_1$ | $Y_2$ | Desirability |
| Constrains | maximum | Maximum | |
| Predicted values | 0.338 | 97.14 | 0.969 |
| Observed values | 0.342 | 97.5 | |

Example-3: Determination of Degree of Substitution (D. S.)

Degree of substitution of carbamoylethyl katira gum was calculated using % nitrogen content of carbamoylethyl katira gum. The % N content was determined by elemental analyser. The DS was measured using following formula:

$$DS = \frac{162 \times \% N}{1400 - (71 \times \% N)}$$

Example-4: Characterization of Carbamoylethyl Katira

A. The FTIR spectra of dried Katira gum or derivatized Carbamoylethyl Katira samples were recorded on ATR-FTIR spectrophotometer (Bruker, alfa E, Germany). The dry powder was used for spectral analysis. FTIR spectra were scanned in the wavelength range of 400-4000 cm$^{-1}$.

B. DSC measurements were performed on powdered samples of Katira gum or Carbamoylethyl Katira gum employing differential scanning calorimeter (812E, Mettler Toledo, Switzerland) in the range of 40 to 350° C. at a heating rate of 10° C./min.

C. The X-ray powder diffraction data was acquired by Analytical Diffractometer (XPERT PRO, PANalyticals, Almelo, Netherlands) equipped with a scintillation counter detector and a divergent beam. Johansson monochromator was used to produce pure Cu k[α]1 radiation (1.5406 A°; 45 kV; 40 mA; range 10°-80° 2θ). The samples were crushed to a fine powder and pressed into a sample holder. X-Ray diffraction data were collected at 25° C. temperature and scanned with a step size of 0.0170 2θ and a scan time of 20 sec at each step.

D. $^1$H NMR spectra was recorded on BRUKER ADVANCE II 400 NMR Spectrometer at 25° C. in $D_2O$. The purified sample was placed in sample probe and the resonance spectrum was obtained. The chemical shifts were reported in ppm relative to an internal standard $D_2O$.

E. Morphological features of the katira gum and Carbamoylethyl Katira were studied with a scanning electron microscope (JSM-6510, Jeol, Tokyo, Japan). The dried sample was mounted on a metal stub and sputtered with gold in order to make the sample conductive and the images were taken at an accelerating voltage of 10 KV and at varied magnification.

F. Molecular weight of carbamoylethyl katira was determined by MALDI TOF Mass Spectroscopy. Carbamoylethyl katira solution (1% w/v, 2 µl) was mixed with 2 µl of the matrix solution (2,5-dihydroxybenzoic acid 10 mg/ml in TFA:CH3CN::1.75:0.75; v/v) and a total of 2 µl of this solution was applied to a stainless steel sample slide and dried under vacuum. MALDI-TOF mass spectra of the carbamoylethyl katira was recorded in reflectron mode using ultraflex TOF/TOF (Bruker Daltonics) MALDI-TOF mass spectrometer equipped with delayed-ion extraction. Spectra from multiple (100) laser shots ($N_2$ laser) were summarised using 25 kV reflectron voltage.

The FTIR spectra of Katira gum showed broad peaks in range of 3000-3500 $cm^{-1}$ which could be due to hydrogen bond stretching vibration (O—H). The characteristic peaks at 1720 $cm^{-1}$ and 1596 $cm^{-1}$ is due carbonyl group stretching of katira gum. The modification of this gum to Carbamoylethyl Katira showed characteristic peaks at 1673 $cm^{-1}$, 1555 $cm^{-1}$, 1405 $cm^{-1}$ and 1013 $cm^{-1}$ indicated chemical linkage of monomer with pure gum. The peak observed at 1555 $cm^{-1}$ is due to amide I band of carbonyl stretching and at 1405 $cm^{-1}$ due to amide II band of N—H bending. The peak observed at 1013 $cm^{-1}$ is due to C—O—C stretching vibration of ether group. A similar peak for this derivatization was observed by Gupta et al., (Gupta, S., Sharma, P., & Soni, P. L. (2005). Chemical modification of Cassia occidentalis seed gum: carbamoylethylation. Carbohydrate polymers, 59(4), 501-506).

The DCS thermogram of katira gum showed two endothermic transitions at 45.786° C. (ΔH=0.422 J/g) and 87.18° C. (ΔH=146.962 J/g) and one exothermic transition at 256.962° C. (ΔH=−6.544 J/g). However, the derivatized Carbamoylethyl Katira showed two endothermic transitions at 97.644° C. (ΔH=161.262 J/g) and 233.63° C. (ΔH=32.461 J/g) and one exothermic transition at 265.033° C. (ΔH=−49.802 J/g).

The powdered X-ray diffractions of Katira gum and Carbamoylethyl Katira showed regular pattern of X-ray diffraction of katira gum reflects amorphous nature of pure gum. However, X-ray diffraction pattern of Carbamoylethyl Katira gum showed peaks at 2θ of 16.96°, 20.6°, 22.55°, 25.18°, 29.72°, 30.82°, 36.6° indicating crystalline nature of Carbamoylethyl Katiragum.

In $^1$H NMR spectra of Katira gum chemical shift value at δ 1-3 ppm belongs to secondary hydrogen atoms of side chain attached to galactopyranose ring in polysaccharide unit. The $^1$H NMR spectra of Carbamoylethyl Katira gum showed multiple splitting of peak sin region of δ 1-3 ppm suggest increase in number of secondary hydrogen atoms and chemical shift value at 5-7 ppm indicated hydrogen atoms attached to acylaminoand carboxyl gropus. A similar chemical shift values for this derivatiztion was observed by Ren et al., (Ren, J. L., Peng, F., & Sun, R. C. (2008). Preparation of hemicellulosic derivatives with bifunctional groups in different media. Journal of agricultural and food chemistry, 56(23), 11209-11216).

Figure 2:
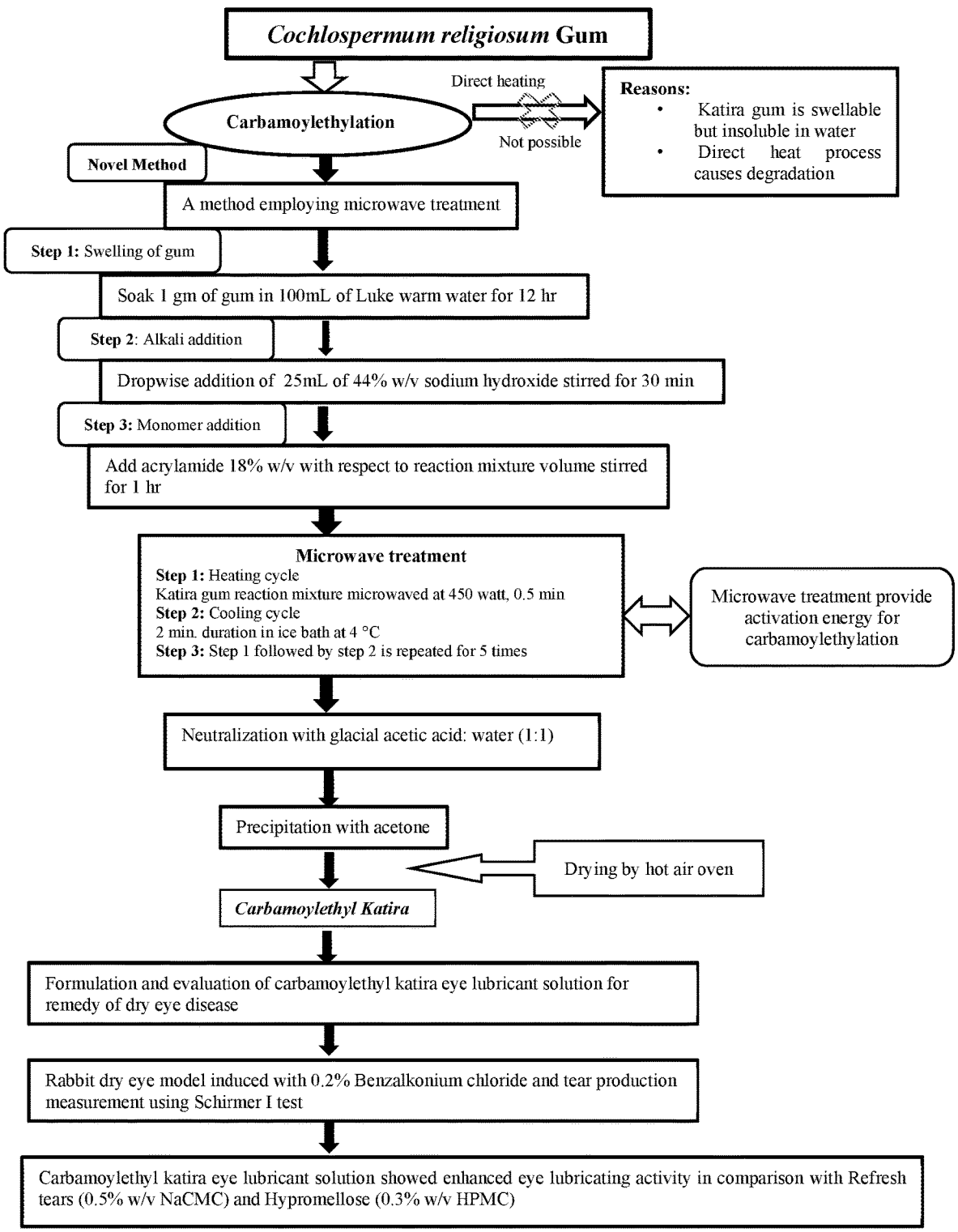
FIG. 2 Illustrates Scanning electron microscopy image of katira gum and carbamoylethyl katira gum FIG. 3 Illustrates viscosity vs time graph for (a) unsterilized carbamoylethyl katira (3% w/v) gum solution; (b) sterilized carbamoylethyl katira (3% w/v) gum solution at constant shear rate (40 s$^{-1}$)

The SEM images suggested irregular shaped particles of katira gum having rough surface. However, SEM images of Carbamoylethyl Katira gum showed crystals of Carbamoylethyl Katira gum (FIG. 2). Thus, the results were in concurrence with XRD spectra studies.

From MALDI-TOF mass spectra of Carbamoylethyl Katira, it has been observed that molecular weight of Carbamoylethyl Katira gum is approximately 1466 g/mol. The fragmentation pattern of Carbamoylethyl Katira gum molecule with their respective m/z value has been shown in Table 3.

TABLE 3

Results of MALDI-TOF of carbamoylethyl katira gum

| m/z value | Fragment |
|---|---|
| 22.899 | $Na^+$ |
| 38.879 | $K^+$ |
| 80.897 | $CH_2COONa$ |
| 137 | $CH_2OCH_2CH_2COO\ K^+$ |
| 393 | →4)α-D-MGalp-(1→4)-α-L-Rhap(1→ |
| 647 | →4)α-D-NaMGalp-(1→4)-α-L-Rhap-α-D-MGalp(1→ |
| 1046 | →4)α-D-MGalp-(1→4)-α-L-Rhap-β-D-NaMGalp-(1→4)-α-L-Rhap-α-D MGalp(1→ |
| 1241 | →4)α-L-Rhap-β-D-NaMGalp-(1→4)-α-L-Rhap-α-D MGalp(1→<br>2        2<br>↑        ↑<br>β-L-Rhap    β-D-NaMGalp |
| 1466 | →4)α-D-MGalp-(1→4)-α-L-Rhap-β-D-NaMGalp-(1→4)-α-L-Rhap-α-D MGalp(1→<br>2        2<br>↑        ↑<br>β-L-Rhap    β-D-NaMGalp |

Galp—galactopyranose,
Rhap—rhamnopyranose,
M—acrylamide monomer attached

Example-5

The carbamoylethyl katira was analyzed for different powder characteristics like bulk and tap densities, Hausner's ratio, Compressibility index, Angle of repose, Swelling capacity and Effective pore radius ($R_{eff-P}$). The Bulk, density, tap density, Hausner's ratio, Cans index, Angle of repose, Swelling capacity and Effective pore radius ($R_{eff-P}$) was found to be 1.18±0.03 g/ml, 1.21±0.03 g/ml, 1.02±0.13, 2.47±0.14, 25.98±0.57, 215±0.12 and 0.0259±0.33 mm, respectively as per mentioned in USP30 NF25.

Example-6: Stability of Carbamoylethyl Katira Gum Solution after Autoclaving Employing ftir-atr The stability of gum solution for its resistance to autoclaving temperature was examined using FTIR-ATR spectral analysis. The sterilized carbamoylethyl katira gum solution (1-10% w/v) was subjected to FTIR-ATR and the spectra obtained were compared with unsterilized carbamoylethyl katira gum solution (1-10% w/v).

The FTIR-ATR spectra of unsterilized 1% w/v gum solution showed peaks at 1216.46 $cm^{-1}$, 1413.53 $cm^{-1}$, 1551.70 $cm^{-1}$, 1644.42 $cm^{-1}$, 1795.36 $cm^{-1}$ and 3236.68 $cm^{-1}$. A similar peaks with enhanced magnitude was observed in FTIR-ATR spectra of gum solutions 5% w/v and 10% w/v. The FTIR-ATR spectra of sterilized 1%, 5%, and 10% w/v carbamoylethyl katira gum solutions showed the similar prominent characteristic peaks at 1515.73 cm$^{-1}$, 1546.42 cm$^{-1}$ and 1461 cm$^{-1}$ indicating the gum solution was stable even after autoclaving.

Example-7: Viscosity Analysis

The carbamoylethyl katira gum solutions of different concentrations were analyzed for viscosity using Cup and bob type viscometer (Model CLTD80/QC Anton Paar Rheolab QC) with CC27 spindle. Sample (19 ml) was packed in the sampler (cup) and then the spindle was lowered into the sampler. Prior to the start of the measurement, temperature was maintained at 25° C. The apparent viscosities in centipoises were measured over a constant shear rate (40 s$^{-1}$). The viscosity analysis of carbamoylethyl katira gum solutions (3% w/v and 5% w/v) before and after sterilization was performed with cup and bob type viscometer (Model CLTD80/QC Anton paar Rheolab QC).

Figure 3:
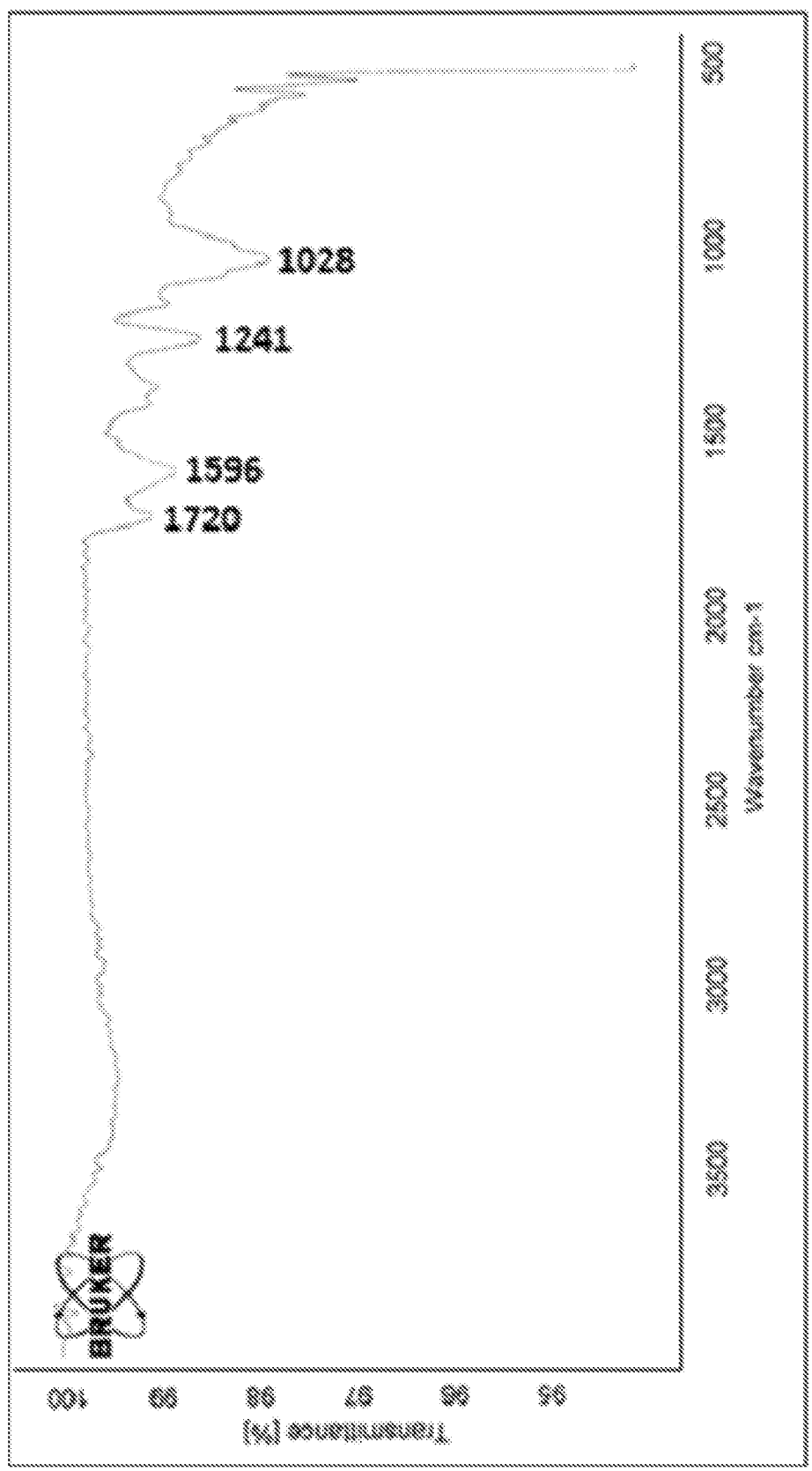
Figure 4:
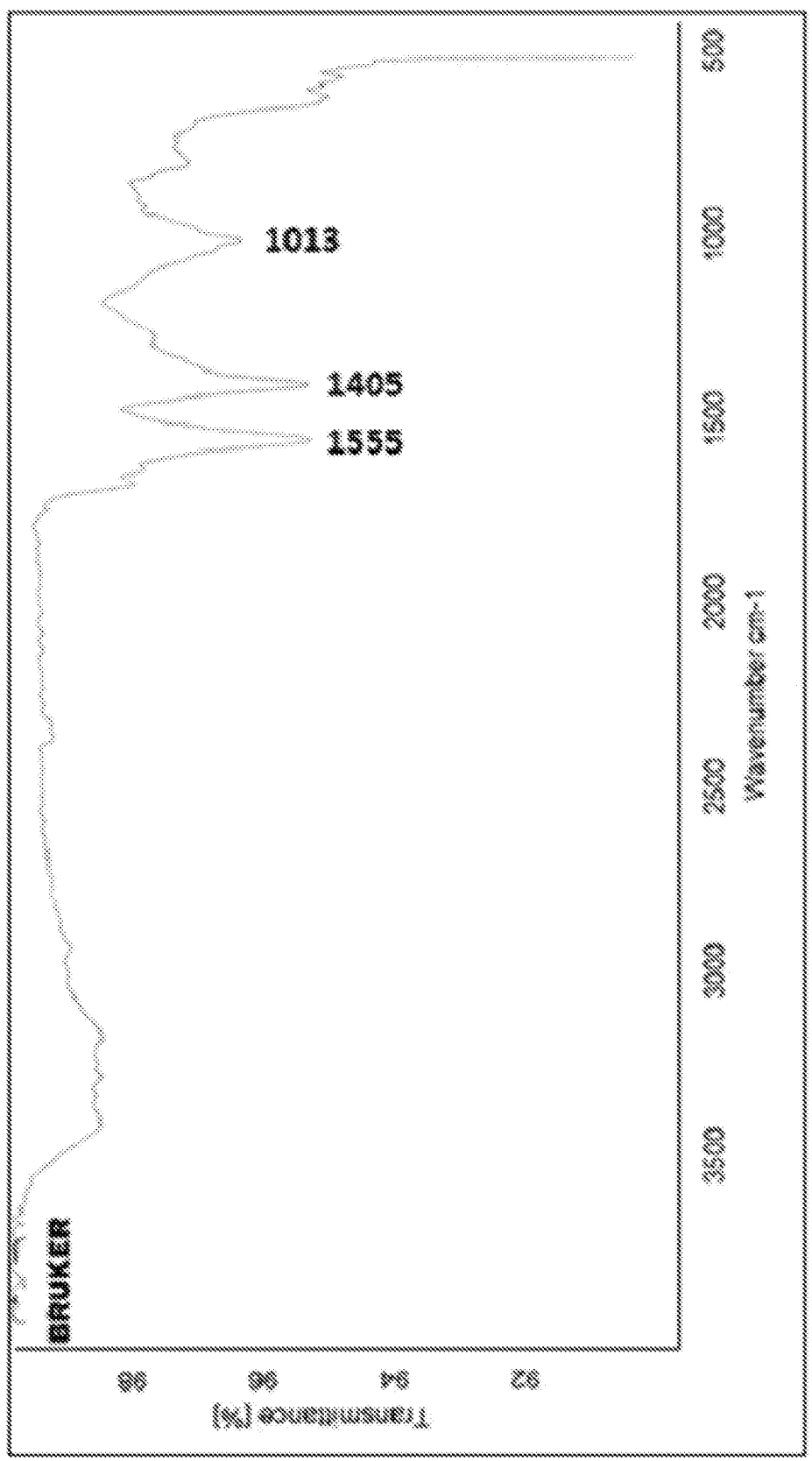
FIG. 4 Illustrates viscosity vs time correlation for (a) unsterilized carbamoylethyl katira (5% w/v) gum solution; (b) sterilized carbamoylethyl katira (5% w/v) gum solution at constant shear rate (40 s$^{-1}$)

The viscosity vs time plots generated at different concentrations was shown in FIGS. 3 to 4. The results suggested thixotropic behaviour of unsterilized 3% w/v and 5% w/v carbamoylethyl katira solution. However, sterilized 3% w/v carbamoylethyl katira solution showed rheopaxy behaviour, whereas 5% w/v carbamoylethyl katira solution maintained thixotropic behaviour even after sterilization.

As a matter of fact, it has been shown experimentally that an ophthalmic solution, in order to have a prolonged residence time on the corneal surface while being, at the same time, well tolerated by the patient must not have a constant viscosity as newtonian fluids do but must behave as a non-newtonian thixotropic behaviour i.e. it must show a decrease of viscosity with increasing shear rate. Only such type of rheology may offer a high viscosity in the precorneal tear film at rest, so that in the absence of any stress the film adheres on the corneal surface without dropping and at the same time may provide a low viscosity in the tear film during a blinking movement, when the film is subjected to a shear stress, so that the ophthalmic solution is well tolerated and is distributed by blinking on the whole corneal surface without being massively displaced due to friction towards the lower eyelid rim as shown by tamarind seed polysaccharide based ophthalmic solution (Saettone, M. F., Burgalassi, S., Giannaccini, B., Boldrini, E., Bianchini, P., & Luciani, G. (2000). U.S. Pat. No. 6,056,950. Washington, D.C.: U.S. Patent and Trademark Office).

Example-8: Texture Analysis

Back extrusion (BE) and cone penetration mechanical test were performed for investigating the descriptors of rheological behavior of carbamoylethyl katira gum solution. Both experiments were performed using a TA XT Plus Texture Analyzer (Stable Micro Systems Ltd., Godalming, U.K.)

The results obtained from texture analysis of different concentrations of carbamoylethyl katira gum solution employing back extrusion ring is shown Table 4. The firmness, consistency, cohesiveness and index of viscosity of carbamoylethyl katira gum solution was increased with increase in concentration of carbamoylethyl katira. The results showed highest firmness and consistency of unsterilized 5% and 10% w/v concentrations. The negative region of graph represents work of cohesion and index of viscosity. The higher is the value, the more resistance to withdraw the sample. Thus, this is a reflection of viscosity of sample. The maximum wok of cohesion and index of viscosity was found to be for 5% and 10% w/v concentrations. However, an insignificant difference (p>0.05) was observed when rheological predictors were compared with sterile samples to unsterilized samples. Thus, carbamoylethyl katira gum is stable and suitable for use in delivery systems even after sterilization.

Table 4 of Rheological Description Evaluated Using Back Extrusion Ring

| Gum solutions | Firmness (N) | Consistency (Ns) * 10$^1$ | Cohesiveness (N) | Index of viscosity (Ns) |
| --- | --- | --- | --- | --- |
| CEKG (1%)$_u$ | 22.36 ± 0.20 | 54.27 ± 0.31 | −13.93 ± 0.50 | −3.75 ± 0.30 |
| CEKG (5%)$_u$ | 28.63 ± 0.32 | 66.98 ± 0.48 | −24.37 ± 0.39 | −6.07 ± 0.35 |
| CEKG (10%)$_u$ | 57.54 ± 0.20 | 166.751 ± 0.50 | −30.65 ± 0.27 | −7.36 ± 0.42 |
| CEKG (1%)$_s$ | 19.27 ± 0.40 | 52.19 ± 0.20 | −13.72 ± 0.22 | −3.21 ± 0.24 |
| CEKG (5%)$_s$ | 24.46 ± 0.22 | 65.02 ± 0.29 | −22.97 ± 0.30 | −5.10 ± 0.51 |
| CEKG (10%)$_s$ | 54.89 ± 0.40 | 163.59 ± 0.37 | −28.46 ± 0.42 | −7.20 ± 0.23 |

CEKG = carbamoylethlated katira gum,
u = unsterilized,
s = sterilized

Example-9: In-Vitro Evaluation of Antimicrobial Activity of Carbamoylethyl Katira/Carboxymethyl Katira Gum Solution Against *Staphylococcus Aureus*

The in vitro antimicrobial activity of carbamoylethyl katira/carboxymethyl katira gum was examined against *Staphylococcus aureus*. The carbamoylethyl katira/carboxymethyl katira gum derivatives were tested for bacteriostatic and bactericidal activity.

Preparation of 24 hr Old Culture of *Staphylococcus aureus*

The pure bacterial strains (*Staphylococcus aureus*) were obtained from Department of Biotechnology, Punjabi University, Patiala. For the preparation of 24 hr old culture, sterile nutrient broth was prepared by mixing definite amount of peptone (5% w/v), yeast extract (2% w/v), beef extract (1% w/v) and sodium chloride (5% w/v) in distilled water, pH adjusted to 7.2 as per Indian Pharmacopoeia (2010) and autoclaved at 15 psi for 30 minutes. The sterile broth was inoculated with the *Staphylococcus aureus* under aseptic conditions and incubated for 24 hrs at 37° C. to obtain 24 hr old culture.

Bacteriostatic Activity

The bacteriostatic activity of carbamoylethyl katira/carboxymethyl katira was determined by serial dilution in solid media and serial dilution in liquid media methods (Benthley"s "Textbook of Pharmaceutics", EA Rawlins (Editor). London: Casella nsCollier Macmilan Publishers Limited: 516).

Serial Dilution in Liquid Media Method

Various test tubes were prepared each containing 5 ml gum solution (1-10% w/v), 24 hr old culture broth of *S. aureus* (0.5 ml), sterilized nutrient broth culture (5 ml). In addition to test samples respective blanks were also prepared. For the test, each test tubes containing gum solution were inoculated with 0.5 ml of *S. aureus* culture broth then 1 ml of inoculated gum solution was transferred into test tubes containing 5 ml nutrient broth culture after 4 hr, 12 hr and 24 hr time interval and these test tubes were incubated for 24 hr at 37° C. The growth was examined by measuring the absorbance of sample at 540 nm against a blank containing nutrient broth culture (5 ml) and 1 ml respective gum solution (without inoculum). The microbial inhibition effect was calculated as follows;

$$\text{Inhibition effect \%} = \frac{(Ac - As)}{Ac} \times 100 \text{ where,}$$

$Ac$ = Absorbance of control, $As$ = Absorbance of sample

Serial Dilution in Solid Media Method

Stock solution of Mannitol Salt agar medium were prepared by dissolving 38 g of media into one litre of lukewarm distilled water in a conical flask. The prepared culture media and petriplates were sterilized separately at 15 psi for 30 minutes. Gum solutions of concentrations (1-10%) were also prepared. 5 ml of gum solution (each concentration) was added in 15 ml of sterilized Mannitol salt agar base media and poured in to the petriplates (90 mm×15 mm) till solidify under aseptic conditions. A suspension of overnight culture of *S. aureus* was spreaded over medium. Plates were incubated (37° C.; 24 h) and observed for visible growth.

Bactericidal Activity

The bactericidal activity of carbamoylethyl katira/carboxymethyl katira was estimated by end point or extinction time method (Benthley"s "Textbook of Pharmaceutics", EA Rawlins (Editor). London: Casella nsCollier Macmilan Publishers Limited: 518-523). There were two types of extinction method employed: (a) In which extinction time is fixed, concentration of bactericidal agent needed to kill in the specific time is estimated (b) In which concentration of bactericidal is fixed, extinction time is estimated. Various test tubes were prepared each containing 2.5 ml gum solution (1-10% w/v), 24 hr old culture broth of *S. aureus* and test samples with respective blanks were prepared. In addition to test samples respective blanks were also prepared. Test tubes containing gum solution were inoculated with 2.5 ml of *S. aureus* culture broth. The growth was examined by measuring the absorbance of sample at 540 nm against a blank containing respective gum solution (without inoculum) after 15 min, 30 min, 45 min, 1 hr, 2 hr and 3 hr incubation. The bactericidal effect was calculated as follows;

$$\text{Bactericidal effect \%} = \frac{(Ac - As)}{Ac} \times 100 \text{ where,}$$

$Ac$ = Absorbance of control, $As$ = Absorbance of sample

The extinction time was the time last growth at which 100% bactericidal effect was first obtained at the fixed concentration of carbamoylethyl katira/carboxymethyl katira gum. The minimum inhibitory concentration (MIC) is the concentration of carbamoylethyl katira/carboxymethyl katira at lowest extinction time. Mean death time for carbamoylethyl katira/carboxymethyl katira gum was calculated by:

$$MDT = \frac{\Sigma \text{ Extinction time}}{\text{No. of extinction time}}$$

TABLE 5

Results of Bacteriostatic activity of carbamoylethyl/carboxyethyl katira gum against *Staphylococcus aureus* using Serial dilution in liquid media method

| Gum solution code | | Bacteriostatic activity against *Staphylococcus aureus* | | | | | |
|---|---|---|---|---|---|---|---|
| | | 4 hr | | 12 hr | | 24 hr | |
| | | Abs | % IE | Abs | % IE | Abs | % IE |
| CEKG | 1% | 0.086 ± 0.03 | 37.45 ± 0.01 | 0.073 ± 0.02 | 64.04 ± 0.02 | 0.063 ± 0.03 | 80.25 ± 0.01 |
| | 5% | 0.061 ± 0.02 | 55.63 ± 0.01 | 0.032 ± 0.01 | 84.23 ± 0.04 | 0.0032 ± 0.03 | 98.99 ± 0.03 |
| | 10% | 0.031 ± 0.02 | 77.45 ± 0.03 | 0.027 ± 0.01 | 86.69 ± 0.01 | 0.0013 ± 0.05 | 99.59 ± 0.03 |
| CMKG | 1% | 0.095 ± 0.05 | 30.9 ± 0.02 | 0.091 ± 0.03 | 55.17 ± 0.01 | 0.067 ± 0.01 | 78.99 ± 0.01 |
| | 5% | 0.063 ± 0.01 | 54.18 ± 0.02 | 0.039 ± 0.04 | 80.78 ± 0.03 | 0.0038 ± 0.01 | 98.80 ± 0.02 |
| | 10% | 0.032 ± 0.01 | 76.72 ± 0.01 | 0.029 ± 0.02 | 85.71 ± 0.05 | 0.0017 ± 0.04 | 99.46 ± 0.02 |
| Control | | 0.137 ± 0.04 | — | 0.203 ± 0.02 | — | 0.319 ± 0.02 | — |

Abs = absorbance,
% IE = percentage inhibition,
CEKG = carbamoylethlated katira gum,
CMKG = carboxymethylated katira gum The in vitro antimicrobial activity of carbamoylethyl katira/carboxymethyl katira gum was examined against *Staphylococcus aureus*. The bacteriostatic activity of carbamoylethyl katira/carboxymethyl katira was determined by serial dilution in solid media and serial dilution in liquid media methods. The bactericidal activity of carbamoylethyl katira/carboxymethyl katira was estimated by end point or extinction time method. The magnitude of absorbance obtained was the indicator of growth of bacteria. The depression in the magnitude of absorbance with time revealed decrease in growth of *Staphylococcus aureus*, irrespective of concentration of carbamoylethyl katira/carboxymethyl katira added into the broth media (Table 5). This suggested both derivatives bear bacteriostatic activity. However, the intensity of effect was found to be enhanced when carbamoylethyl katira 5% w/v to 10% w/v solution was used. To further confirm bacteriostatic activity, a serial dilution in solid media was also used. The CFU was found to be decreased with increase in concentration of carbamoylethyl katira/carboxymethyl katira. The CFU were found to be zero when 5% w/v carbamoylethyl katira/carboxymethyl katira was added in agar media. From the results it could be envisaged that carbamoylethyl katira shown enhanced bacteriostatic activity than DP-I. Thus, the findings assure that 5% w/v carbamoylethyl katira

Example-10: Antioxidant Activity

A. DPPH Radical Scavenging Assay

DPPH radical scavenging effect of carbamoylethyl katira/carboxymethyl katira was determined by the method reported by (Xiong, X., Li, M., Xie, J., Jin, Q., Xue, B., & Sun, T. (2013). Antioxidant activity of xanthan oligosaccharides prepared by different degradation methods. Carbohydrate polymers, 92(2), 1166-1171). In brief, 2.0 ml of ethanolic solution of DPPH (0.1 mmol/l) was incubated with carbamoylethyl katira/carboxymethyl katira gum solution at

TABLE 6

Results of Bactericidal activity of carbamoylethyl/carboxyethyl katira gum against *Staphylococcus aureus* using End point or Extinction point method

| Gum solution code | | Bactericidal activity against *Staphylococcus aureus* | | | | | | | |
|---|---|---|---|---|---|---|---|---|---|
| | | 15 min | | 30 min | | 45 min | | 60 min | |
| | | Abs | % BE | Abs | % BE | Abs | % BE | Abs | % BE |
| CEKG | 1% | 0.096 ± 0.01 | 31.03 ± 0.03 | 0.092 ± 0.02 | 58.74 ± 0.01 | 0.086 ± 0.03 | 78.39 ± 0.02 | 0.081 ± 0.03 | 80.74 ± 0.01 |
| | 5% | 0.062 ± 0.03 | 59.32 ± 0.02 | 0.028 ± 0.02 | 87.44 ± 0.01 | 0.0016 ± 0.03 | 99.59 ± 0.05 | 0 | 100 ± 0.01 |
| | 10% | 0.034 ± 0.03 | 69.85 ± 0.04 | 0.012 ± 0.01 | 94.61 ± 0.03 | 0.0013 ± 0.01 | 99.67 ± 0.03 | 0 | 100 ± 0.04 |
| CMKG | 1% | 0.112 ± 0.04 | 20.28 ± 0.01 | 0.107 ± 0.03 | 52.01 ± 0.02 | 0.102 ± 0.03 | 74.37 ± 0.02 | 0.095 ± 0.01 | 77.21 ± 0.02 |
| | 5% | 0.069 ± 0.02 | 53.85 ± 0.01 | 0.032 ± 0.03 | 85.65 ± 0.03 | 0.0019 ± 0.01 | 99.52 ± 0.02 | 0 | 100 ± 0.03 |
| | 10% | 0.037 ± 0.01 | 55.33 ± 0.03 | 0.014 ± 0.02 | 93.72 ± 0.04 | 0.0014 ± 0.04 | 99.64 ± 0.01 | 0 | 100 ± 0.03 |
| Control | | 0.141 ± 0.01 | — | 0.223 ± 0.01 | — | 0.398 ± 0.02 | — | 0.417 ± 0.01 | — |

| Gum solution code | | Bactericidal activity against *Staphylococcus aureus* | | | | Extinction time (min) | MIC (%) |
|---|---|---|---|---|---|---|---|
| | | 120 min | | 180 min | | | |
| | | Abs | % BE | Abs | % BE | | |
| CEKG | 1% | 0.073 ± 0.01 | 85.34 ± 0.02 | 0.058 ± 0.03 | 89.69 ± 0.03 | >180 | 5% |
| | 5% | 0 | 100 ± 0.02 | 0 | 100 ± 0.03 | 30 | w/v |
| | 10% | 0 | 100 ± 0.01 | 0 | 100 ± 0.01 | 30 | |
| CMKG | 1% | 0.083 ± 0.01 | 83.33 ± 0.03 | 0.071 ± 0.03 | 87.38 ± 0.04 | >180 | 5% |
| | 5% | 0 | 100 ± 0.03 | 0 | 100 ± 0.01 | 30 | w/v |
| | 10% | 0 | 100 ± 0.04 | 0 | 100 ± 0.01 | 30 | |
| Control | | 0.498 ± 0.03 | — | 0.563 ± 0.01 | — | — | — |

Abs = absorbance.
% IE = bactericidal effect $$\text{Mean death time for } CEKG = \frac{\Sigma Extinction\, time}{No.\, of\, extinction\, time} = \frac{30+30}{2} = 30 \text{ min}$$

$$\text{Mean death time for } CMKG = \frac{\Sigma Extinction\, time}{No.\, of\, extinction\, time} = \frac{30+30}{2} = 30 \text{ min}$$

and 5% w/v DP-I was effective bacteriostatic agents. The bactericidal activity of carbamoylethyl katira/carboxymethyl katira was determined using end point or extinction time method. The data obtained summarized in Table 6. carbamoylethyl katira and carboxymethyl katira was found to show minimum inhibitory concentration (MIC) of 5% w/v as no growth was observed. The time taken to attain minimum inhibitory concentration (MIC) was found to be 45 minute (extinction time) suggesting both carbamoylethyl katira and carboxymethyl katira had equally effective bactericidal activity. Therefore, formulations of carbamoylethyl katira (5% w/v) and carboxymethyl katira (5% w/v) was prepared for the effective treatment of bacterial infections caused by *Staphylococcus aureus*.

different concentrations (0.1-10.0 mg/ml, 2.0 ml). The reaction mixture was mixed with vortex shaker, incubated (30 min at 30° C.) and the absorbance of the resulting solution was read at 517 nm against a blank. The DPPH radical scavenging effect was measured as:

$$\% \text{ Scavenging effect} = \frac{1 - absorbance\, of\, sample\, solution\,(517\text{ nm})}{absorbance\, of\, control\, solution\,(517\text{ nm})} \times 100$$

B. Hydrogen Peroxide Scavenging Assay

The activity of carbamoylethyl katira/carboxymethyl katira to scavenge $H_2O_2$ was determined according to the method of (Xiong, X., Li, M., Xie, J., Jin, Q., Xue, B., & Sun, T. (2013). Antioxidant activity of xanthan oligosaccharides prepared by different degradation methods. Carbohydrate polymers, 92(2), 1166-1171). A solution of $H_2O_2$ (40 mM) was prepared in $Na_2HPO_4$—$NaH_2PO_4$ buffer solution (pH=7.40, 0.2 mol/l). $H_2O_2$ concentration was determined spectrophotometrically from absorption at 230 nm. Different concentrations of samples (0.1-10.0 mg/ml) in distilled water were added to a $H_2O_2$ solution (0.6 ml, 40 mM). Absorbance of $H_2O_2$ at 230 nm was determined after 10 min against a blank solution containing phosphate buffer without $H_2O_2$. The activity of all samples to scavenge $H_2O_2$ was calculated using:

$$\% \ Scavenging \ effect = \frac{1 - absorbance \ of \ sample \ solution (230 \ nm)}{absorbance \ of \ control \ solution (230 \ nm)} \times 100$$

Figure 5:
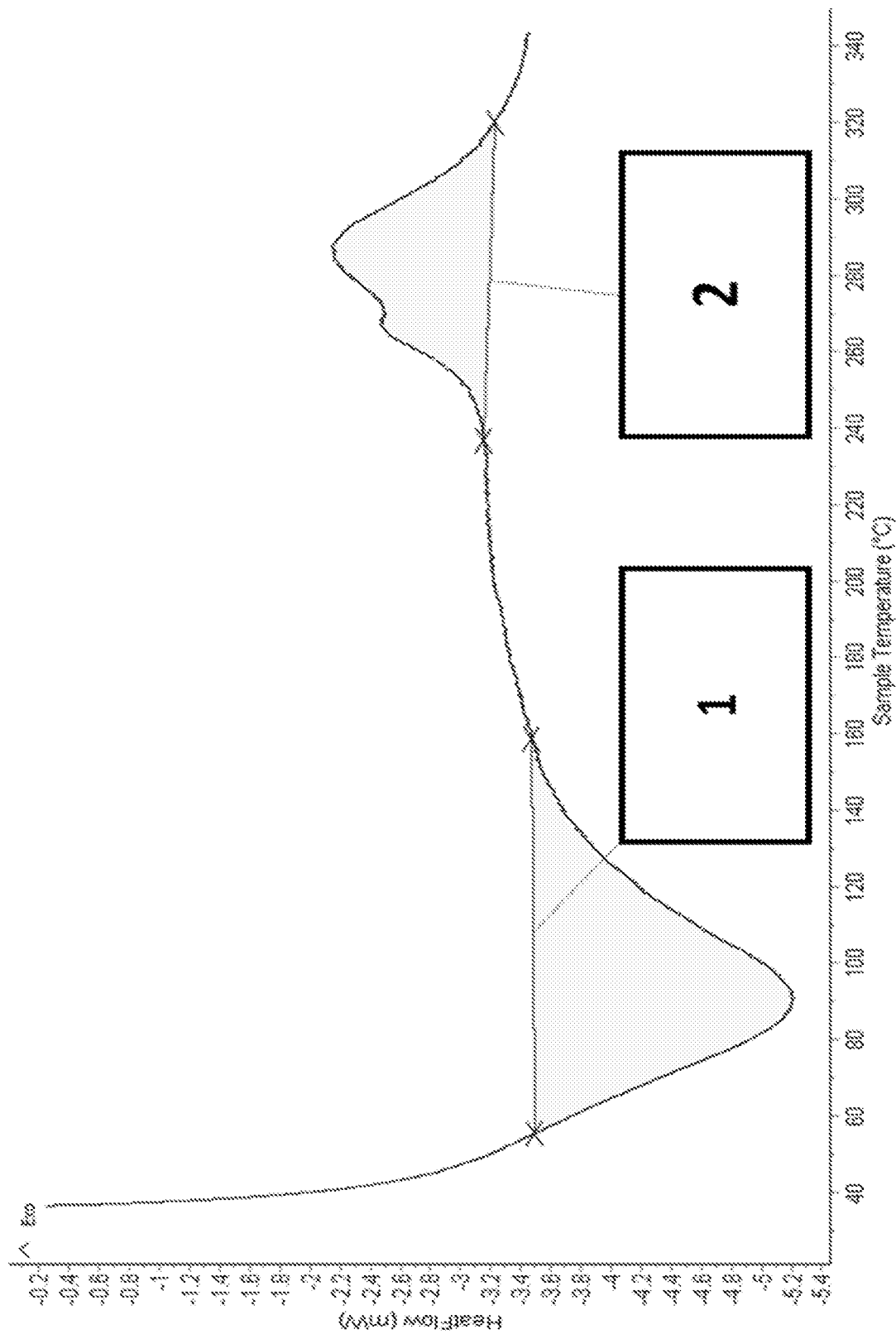
FIG. 5 illustrates antioxidant activity of DPPH carbamoylethyl katira/carboxymethyl katira gum solution (a) DPPHfree radical scavenging activity; (b) Hydrogen peroxide scavenging activity. Data box 1—Heat: 238.769 J/g; T: 55.34 and 158.58 ° C.; t: 154.8 and 756.2 s; Peak Maximum: 90.738 ° C. / 353.2 s; Peak Height: -1.725 mW; Onset 58.153 ° C. / 169.524 s; Offset 120.076 ° C. / 527.214 s; Baseline Type: Linear. Data box 2—Heat: -120.781 J/g; T: 236.92 and 319.99 ° C.; t: 1,223.0 and 1,718.6 s; Peak Maximum: 287.241 ° C. / 1,523 s; Peak Height: 1.502 mW; Onset 256.837 ° C. / 1,341.872 s; Offset 307.431 ° C. / 1,643.572 s; Baseline Type: Linear.

DPPH radical is one of the compounds that possessed a proton free radical with a characteristic absorption, which decreased significantly on exposure to proton radical scavengers. Further, it is well accepted that the DPPH radical scavenging by antioxidants is due to their hydrogen-donating ability. In this experiment, the purple color of the reaction mixture changes to yellow and its absorbance at 517 nm decreases in the presence of antioxidant samples. The results of DPPH free radical scavenging activity and hydrogen peroxide scavenging activity of carbamoylethyl katira/carboxymethyl katira gum solution showed in FIG. 5. The DPPH free radical scavenging activity was found to increase with increase in concentration of carbamoylethyl katira/carboxymethyl katira. From FIG. 5 it had been found that $IC_{50}$ value for carbamoylethyl katira and carboxymethyl katira are about 3 mg/ml and 3.2 mg/ml, respectively. Thus, the derivatization of gum did not affect antioxidant activity. Further, it could be envisaged that the antioxidant activity was related with back bone of gum and not with attachment of groups via derivatization. This suggested derivatization of gum increases the solubility and antioxidant activity. These two factors jointly influence antimicrobial activity.

Example-11: Fabrication and Evaluation of Eye Lubricant Formulations Using Carbamoylethyl Katira/Carboxymethyl Katira Eye solutions of different concentrations (2.5%-10%) of carbamoylethyl katira/carboxymethyl katira were prepared in sterile water for injection (Table 7). The pH of eye solutions was adjusted to 7.4 and isotonicity was adjusted using Sodium chloride Equivalent method. The prepared eye solutions were filled in previously cleaned, sterilizable bottles after filtered through a 0.22 μm pore size filter and sterilized by autoclaving (15 psi, 30 mM.) All the formulations are evaluated for appearance, specific gravity, viscosity and surface tension. Sodium chloride was used to make isotonic formulations.

TABLE 7

Various eye drop formulations of Carbamoyl ethyl Katira/carboxymethyl katira gum

| Eye drop formulations code | Solvent | Concentration of carbamoylethyl katira (CEKG)/ carboxymethyl katira (CMKG) gums | pH adjusted | Final volume of eye drop formulations |
|---|---|---|---|---|
| $E_1$ | Sterile water for injection | CEKG - 2.5% | 7.4 | 100 ml |
| $E_2$ | Sterile water for injection | CEKG - 5% | 7.4 | 100 ml |
| $E_3$ | Sterile water for injection | CEKG - 7.5% | 7.4 | 100 ml |
| $E_4$ | Sterile water for injection | CEKG - 10% | 7.4 | 100 ml |
| $E_5$ | Sterile water for injection | CMKG - 2.5% | 7.4 | 100 ml |
| $E_6$ | Sterile water for injection | CMKG - 5% | 7.4 | 100 ml |
| $E_7$ | Sterile water for injection | CMKG - 7.5% | 7.4 | 100 ml |
| $E_8$ | Sterile water for injection | CMKG - 10% | 7.4 | 100 ml |

The developed eye lubricant formulations were sterilized in autoclave (121° C.; 15 psi; 20 min) after transferring into polypropylene eye drop containers having variable pore size of orifice for dispensing eye drops. The eye lubricant formulations obtained after autoclaving was tested for specific gravity, viscosity and surface tension. The results of physical evaluation of eye lubricant formulations are shown in Table 8. All the formulations E1 to E8 were clear and absence of any visible particulate matter

TABLE 8

Physical properties of different eye lubricant solutions

| Eye lubricants code | pH observed | Specific gravity (g/cm³) | Viscosity (mPa · s) | Surface tension (mN/m) |
|---|---|---|---|---|
| $E_1$ | 7.4 ± 0.2 | 1.013 ± 0.2 | 4.25 ± 0.2 | 39.8 ± 1.0 |
| $E_2$ | 7.4 ± 0.2 | 1.016 ± 0.3 | 6.50 ± 0.3 | 42.7 ± 1.2 |
| $E_3$ | 7.3 ± 0.1 | 1.02 ± 0.2 | 8.75 ± 0.5 | 54.2 ± 1.2 |
| $E_4$ | 7.2 ± 0.3 | 1.025 ± 0.4 | 9.50 ± 0.2 | 59.1 ± 0.9 |
| $E_5$ | 7.4 ± 0.1 | 1.012 ± 0.2 | 4.19 ± 0.4 | 40.2 ± 1.3 |
| $E_6$ | 7.4 ± 0.4 | 1.013 ± 0.2 | 5.93 ± 0.3 | 45.3 ± 1.1 |
| $E_7$ | 7.2 ± 0.2 | 1.015 ± 0.2 | 8.13 ± 0.3 | 60.7 ± 1.4 |
| $E_8$ | 7.1 ± 0.3 | 1.018 ± 0.3 | 9.14 ± 0.1 | 63.5 ± 1.2 |

Example-12: Drop Size Determination of Eye Lubricant Formulations

The drop size of the eye drop formulations was characterised by its weight. A commercially available flexible plastic dropper bottles were filled with 10 ml eye drop formulations and fitted with a two different dropper tips Tip A and Tip B having orifice diameter of 0.45 mm and 0.70 mm, respectively. The orifice diameters of tips were determined by using compound microscope having stage eye piece. The bottle was fixed in the upright position (90° angle) or at an angle of 45° and compressed the bottle until a drop was delivered. The drop was weighed immediately on analytical balance. For each solution, three series of 10 drops were dispensed and the mean weight and standard deviation of the three series were calculated (Van Santvliet, L., & Ludwig, A. (1999). Influence of the physico-chemical properties of ophthalmic viscolysers on the weight of drops dispensed from a flexible dropper bottle. European journal of pharmaceutical sciences, 7(4), 339-345).

Pharmaceutical and Patient Determinants of Eye Drop Size

Selection of Eye Drop Container

An aqueous ophthalmic solution instilled as a drop in lower conjunctiva sac, remains the preferred dosage form for an ocular medication (Lang, J. C. (1995). "Ocular drug delivery conventional ocular formulations." Advanced Drug Delivery Reviews 16(1), 39-43). These solutions are formulated for multidose or single dose administer in wide variety of glass and plastic dropper bottles. The average drop size of ophthalmic solution was assumed to be 50-70 μl (Shell, J. W. (1982). "Pharmacokinetics of topically applied ophthalmic drugs." Survey of Ophthalmology 26(4), 207-21; Urtti, A. and L. Salminen (1993). "Minimizing systemic absorption of topicallyadministered ophthalmic drugs." Survey of Ophthalmology 37(6), 435-456). However, Lederer et al., (Lederer, C. M., Jr. and R. E. Harold (1986). "Drop size of commercial glaucomamedications." American Journal of Ophthalmology 101(6), 691-694) estimated the average drop size of many commercially available topical medications to be 39 μl with a range of 25.1 to 56.4 μl. In addition, ophthalmologist performing studies to find number o drops per dose, cost per dose and cost per bottle eye drop medicament reported eye drop volumes ranging from 26.4 μl up to 69.4 μl (Sorensen, S. J. and S. R. Abel (1994). "Drop size of ocular carteolol hydrochloride." American Journal of Hospital Pharmacy: 51(11), 1470-1473; Stewart, W. C., C. Sine, E. Cate, G. E. Minno and H. H. Hunt (1997). "Daily cost of beta adrenergic blocker therapy." Archives of Ophthalmology 115(7), 853-856). From bioavailability and toxicological points of view, even smaller volume drops of 5 to 15 μl could be administered (Flach, A. (1994). "Systemic toxicity. Associated with topical ophthalmic medications." The Journal of the Florida Medical Association 81(4), 256-260; Urtti, A. and L. Salminen (1993). "Minimizing systemic absorption of topically administered ophthalmic drugs." Survey of Ophthalmology 37(6), 435-456). The size of drops delivered from plastic dropper bottles is influenced by three major factors: The design and characteristics of the dropper tip and bottle, the physico-chemical properties of the solution to be dispensed and patient manner of handling the dropper bottle. Therefore, selection of eye drop container was on the basis of above three major factors.

The Design and Characteristics of the Dropper Tip and Bottle

As per the specifications given by European pharmacopoeia, polyethylene, that is low density polyethylene without or with additives and polypropylene are the required plastic dropper bottles. However, the United State pharmacopoeia does not specify the type of plastic. Therefore, in the present study polypropylene bottles designed for eye drops and available in market were purchased. Another important part of container is plastic tip for drop dispensing. The tip is plugged into the neck of the bottle. Several dropper tip designs are available. The simplest design is a nozzle with small calibrated opening for the passage of the liquid. To prevent a jet when the bottle is squeezed, an elongated narrow central duct can be introduced in the tip design. This ensures a drop by drop dispensing of the liquid. The duct has a wider/outer orifice, where the drop is formed and expelled and a narrow inner aperture. This later controls the flow of the liquid entering the duct. Therefore, the tip having a conical channel (straight narrow cylindrical channel) and the outer orifice located on a hemispherical surface with available diameter was selected for the eye drop formulation.

Effect of Concentration of Eye Solution on Drop Size

Four different concentrations of eye solution containing carbamoylethyl katira (2.5% w/v, 5% w/v, 7.5% w/v and 10% w/v) and carboxymethyl katira (2.5% w/v, 5% w/v, 7.5% w/v and 10% w/v) were examined for their effect on drop size. The results were summarised in Table 9. It was observed that drop weight was significantly increased with increase in concentration of carbamoylethyl katira/carboxymethyl katira. A similar result was observed even when tip size was increased from 0.45 mm to 0.7 mm. The average drop size of ophthalmic solution was reported to be 20-70 μl (USP 30 NF25). Therefore, $E_1$, $E_2$ containing carbamoylethyl katira (2.5% w/v and 5% w/v) and $E_5$, $E_6$ containing carboxymethyl katira (2.5% w/v and 5% w/v) could be the best ophthalmic solution to meet USP standard. The marketed formulations made from HPMC (0.3% w/v) and NaCMC (0.5% w/v) were showed drop size in the range of 20-70 μl that meet USP standard. Interestingly, the amount of carbamoylethyl katira/carboxymethyl katira entrapped in the single eye drop was higher as compared to marketed formulations. Thus, carbamoylethyl katira/carboxymethyl katira can be used for dual purpose i.e. as lubricant as well as antibacterial eye drop.

TABLE 9

Effect of concentration of eye lubricant solution on drop size

| Eye lubricant formulation code | Concentration of eye solution (w/v) | No. of drops | Specific gravity of eye drop solutions | Tip A Orifice size = 45 mm Drop size | | Tip B Orifice size = 70 mm Drop size | |
|---|---|---|---|---|---|---|---|
| | | | | Weight per drop (mg) | Volume per drop (μl) | Weight per drop (mg) | Volume per drop (μl) |
| $E_1$ | CEKG - 2.5% | 10 | 1.013 ± 0.2 | 35.47 ± 1.1 | 35.02 ± 0.3 | 42.84 ± 1.0 | 42.30 ± 0.2 |
| $E_2$ | CEKG - 5% | 10 | 1.016 ± 0.3 | 40.47 ± 0.3 | 39.84 ± 0.6 | 45.90 ± 0.6 | 45.18 ± 0.7 |
| $E_3$ | CEKG - 7.5% | 10 | 1.02 ± 0.2 | 59.30 ± 1.5 | 58.14 ± 0.5 | 64.49 ± 0.3 | 63.23 ± 1.3 |
| $E_4$ | CEKG - 10% | 10 | 1.025 ± 0.4 | 77.14 ± 1.2 | 75.26 ± 1.3 | 81.13 ± 1.1 | 79.16 ± 0.4 |
| $E_5$ | CMKG - 2.5% | 10 | 1.012 ± 0.2 | 40.85 ± 0.4 | 40.37 ± 0.4 | 45.75 ± 1.2 | 45.21 ± 1.2 |
| $E_6$ | CMKG - 5% | 10 | 1.013 ± 0.2 | 45.76 ± 1.0 | 45.18 ± 1.0 | 55.81 ± 0.5 | 55.10 ± 1.1 |
| $E_7$ | CMKG - 7.5% | 10 | 1.015 ± 0.2 | 61.03 ± 0.3 | 60.13 ± 1.1 | 73.25 ± 0.7 | 72.17 ± 1.1 |
| $E_8$ | CMKG - 10% | 10 | 1.018 ± 0.3 | 80.57 ± 0.6 | 79.15 ± 0.3 | 84.72 ± 0.7 | 83.23 ± 0.5 |
| Marketed formulations Hypromellose | HPMC - 0.3% | 10 | 1.02 ± 0.4 | 47.09 ± 0.4 | 46.17 ± 1.5 | 53.19 ± 1.3 | 52.15 ± 0.3 |

TABLE 9-continued

Effect of concentration of eye lubricant solution on drop size

| Eye lubricant formulation code | Concentration of eye solution (w/v) | No. of drops | Specific gravity of eye drop solutions | Tip A Orifice size = 45 mm Drop size | | Tip B Orifice size = 70 mm Drop size | |
|---|---|---|---|---|---|---|---|
| | | | | Weight per drop (mg) | Volume per drop (μl) | Weight per drop (mg) | Volume per drop (μl) |
| Refresh tears | NaCMC - 0.5% | 10 | 1.05 ± 0.3 | 52.17 ± 1.0 | 49.69 ± 1.2 | 58.24 ± 1.2 | 55.47 ± 0.6 |

Physical and Chemical Properties of the Eye Solution

The surface tension and viscosity are the two important physical parameters for ophthalmic solution. The surface tension of ophthalmic solution is a major determination of size of drop. The surface tension of tear fluid has been found to be between 44 mN/m to 50 mN/m and ophthalmic solution should have surface tension equal to surface tension of tear fluid (Desai, H. R. and P. D. Amin (2013). "Cationic submicron emulsion in ocular drug delivery a review." International Journal of Pharma Sciences and Research 3(7), 5499-5511). The results of surface tension of different eye drop formulations are shown in Table 10. The surface tension of $E_1$, $E_2$, $E_5$ and $E_6$ was found to be equivalent to surface tension of tear fluid. According to Tate's law, the lower the surface tension of the solution, smaller the drop dispensed (Van Santvliet, L., & Ludwig, A. (1999). Influence of the physico-chemical properties of ophthalmic viscolysers on the weight of drops dispensed from a flexible dropper bottle. European journal of pharmaceutical sciences, 7(4), 339-345). The linearity in the correlation of drop size and surface tension suggested carbamoylethyl katira/carboxymethyl katira eye drop formulations to obey Tate's law ($r^2$=0.970/0.872, respectively).

ing their medication. Van Santvliet et al., (Van Santvliet, L., & Ludwig, A. (1999). Influence of the physico-chemical properties of ophthalmic viscolysers on the weight of drops dispensed from a flexible dropper bottle. European journal of pharmaceutical sciences, 7(4), 339-345) studied the rheological behaviour, viscoelasticity and surface tension of various viscolysers on the weight of drop dispensed from a commercially available flexible dropper bottle. The results suggested up to a value of 25 mPa·s, the viscosity and the rheological behaviour of the solution had no significant influence on the drop weight under condition simulating patient manipulation. Further, the increase in viscosity of a eye drop solution leads to decrease in benefits as the solution create both discomfort, by resisting eye lid movement during blinking and blurred vision (Dudinski, O., Finnin, B. C., & Reed, B. L. (1983). Acceptability of thickened eye drops to human-subjects. Current Therapeutic Research-Clinical and Experimental, 33(2), 322-337). In general viscous ophthalmic solutions exhibiting to movement of eyelids over the globe and therefore are more comfortable than Newtonian solution (Ludwig, A. (2005). The use of mucoadhesive polymers in ocular drug delivery. Advanced drug delivery reviews, 57(11), 1595-1639). The viscosity of all the eye

TABLE 10

Effect of surface tension on drop size dispensed from a plastic dropper bottle

| Eye lubricant formulation code | Concentration of eye solution (w/v) | Surface tension (mN/m) | Viscosity (mPa · s) | Tip A Orifice size = 45 mm Drop size (μl) | Tip B Orifice size = 70 mm Drop size (μl) |
|---|---|---|---|---|---|
| $E_1$ | CEKG - 2.5% | 39.8 ± 1.0 | 4.25 ± 0.2 | 35.02 ± 0.3 | 42.30 ± 0.2 |
| $E_2$ | CEKG - 5% | 42.7 ± 1.2 | 6.50 ± 0.3 | 39.84 ± 0.6 | 45.18 ± 0.7 |
| $E_3$ | CEKG - 7.5% | 54.2 ± 1.2 | 8.75 ± 0.5 | 58.14 ± 0.5 | 63.23 ± 1.3 |
| $E_4$ | CEKG - 10% | 59.1 ± 0.9 | 9.50 ± 0.2 | 75.26 ± 1.3 | 79.16 ± 0.4 |
| $E_5$ | CMKG - 2.5% | 40.2 ± 1.3 | 4.19 ± 0.4 | 40.37 ± 0.4 | 45.21 ± 1.2 |
| $E_6$ | CMKG - 5% | 45.3 ± 1.1 | 5.93 ± 0.3 | 45.18 ± 1.0 | 55.10 ± 1.1 |
| $E_7$ | CMKG - 7.5% | 60.7 ± 1.4 | 8.13 ± 0.3 | 60.13 ± 1.1 | 72.17 ± 1.1 |
| $E_8$ | CMKG - 10% | 63.5 ± 1.2 | 9.14 ± 0.1 | 79.15 ± 0.3 | 83.23 ± 0.5 |
| Marketed formulations Hypromellose | HPMC-0.3% | 45.8 ± 1.1 | 10.15 ± 0.1 | 46.17 ± 1.5 | 52.15 ± 0.3 |
| Refresh tears | NaCMC-0.5% | 47.2 ± 1.5 | 13.29 ± 0.3 | 49.69 ± 1.2 | 55.47 ± 0.6 |
| Specification as per literature (Desai et al., 2013) | — | 44 to 50 mN/m | upto 25 mPa · s | | |

This suggested the eye drop solution prepared with carbamoylethyl katira (5% w/v, 2.5% w/v) or carboxymethyl katira (5% w/v, 2.5% w/v) could be the ideal solution for the preparation of eye drop formulations. When dispensing the smaller drops of lower surface tension solution, less force needed to be exerted on the bottle and a lower dispensing time was noted. This could be also a practical advantage for elderly people experiencing physical difficulties with instilldrop formulations was found to be less than 25 mPa·s including marketed formulations. In addition, there was no significant difference (P>0.05) in the viscosities of carbamoylethyl katira/carboxymethyl katira. However, viscosity of marketed formulations Hypromellose (HPMC 0.3% w/v) and refresh tears (NaCMC 0.5% w/v) was higher than carbamoylethyl katira/carboxymethyl katira, but less than 25 mPa·s. Further, the drop size of eye drop solution was found to increase with increase in viscosity of formulation. The linear correlation of viscosity with drop size of eye drop solution containing carbamoylethyl katira/carboxymethyl katira was not affected by increase in size of orifice. The viscosity of NaCMC (1% w/v) and HPMC (1% w/v) was reported to be 19.8 mPa·s and 23.4 mPa·s, respectively (Van Santvliet, L., & Ludwig, A. (1999). Influence of the physico-chemical properties of ophthalmic viscolysers on the weight of drops dispensed from a flexible dropper bottle. European journal of pharmaceutical sciences, 7(4), 339-345). However, the viscosity of carbamoylethyl katira/carboxymethyl katira was less than 25 mPa·s even when used in 10% w/v concentration. Thus, the carbamoylethyl katira/carboxymethyl katira could be effectively used for treatment of dry eyes and other bacterial infections at their MIC level. Therefore, eye drop formulations $E_1$ (carbamoylethyl katira 2.5% w/v), $E_2$ (carbamoylethyl katira 5% w/v), $E_5$ (carboxymethyl katira 2.5% w/v) and $E_6$ (carboxymethyl katira 5% w/v) were selected for further study.

Effect of Dispensing Angle/Tilting

When instilling an eye drop, the patient has to hold the dropper at a 90° angle above his eye, but in practice this angle varies from 90° to 30° (Van Santvliet, L., & Ludwig, A. (1999). Influence of the physico-chemical properties of ophthalmic viscolysers on the weight of drops dispensed from a flexible dropper bottle. European journal of pharmaceutical sciences, 7(4), 339-345). To investigate the influence of the angle at which a dropper bottle is held, the drop weight of $E_1$-$E_8$ eye drop solution formulation was measured with apparatus positioned at 90° to 45° angle. The results of these measurements are shown in Table 11.

Example-13: In-Vitro Antimicrobial Activity of Eye Lubricant Formulations

The in vitro antimicrobial activity of carbamoylethyl katira (2.5% w/v, 5% w/v)/carboxymethyl katira (2.5% w/v, 5% w/v) eye drop formulations was examined against *Staphylococcus aureus* using agar well diffusion method as per method reported in Indian Pharmacopoeia (2010).

Preparation of 24 hr Old Culture

For the preparation of 24 hr old culture, sterile nutrient broth was prepared by mixing definite volumes of peptone (0.6%), yeast extract (0.15%) and di-potassium dihydrogen phosphate (0.36%) in distilled water, pH adjusted to 7.2 (I.P 2010) and autoclaved at 15 psi for 30 minutes. The sterile broth was inoculated with the *Staphylococcus aureus* under aseptic conditions and incubated for 24 hrs at 37° C. to obtain 24 hr old culture.

Agar Well Diffusion Method for the Determination of Antimicrobial Activity 23 grams of solid media was dissolved in one litre of lukewarm distilled water in a conical flask. The prepared culture media and petriplates were sterilized separately at 15 psi for 30 minutes. The 1 ml of 24 hr old microbial suspension was added to sterilized nutrient agar media at 40° C. and poured in to the petriplates (90 mm×15 mm) till solidify under aseptic conditions. The wells were prepared with the help of sterile borer. For each petriplate four wells were created. Each of the well was filled with 0.5 ml of eye drop formulations. After incubation at 37° C. for 24 hrs, the zones of inhibition were recorded.

TABLE 11

The effect on mean drop size of carbamoylethyl/carboxyethyl katira gum eye lubricant solution when dispensed at an angle 45° and 90°

| Eye lubricant formulation | | Concentration of eye | Tip A Orifice size = 0.45 mm Drop size (µl) | | Tip B Orifice size = 0.70 mm Drop size (µl) | |
|---|---|---|---|---|---|---|
| | code | solution (w/v) | 45° | 90° | 45° | 90° |
| | $E_1$ | CEKG - 2.5% | 34.15 ± 0.5 | 35.02 ± 0.3 | 40.68 ± 0.4 | 42.30 ± 0.2 |
| | $E_2$ | CEKG - 5% | 37.23 ± 0.3 | 39.84 ± 0.6 | 43.71 ± 0.2 | 45.18 ± 0.7 |
| | $E_3$ | CEKG - 7.5% | 57.31 ± 0.3 | 58.14 ± 0.5 | 62.56 ± 0.2 | 63.23 ± 1.3 |
| | $E_4$ | CEKG - 10% | 73.69 ± 0.6 | 75.26 ± 1.3 | 78.02 ± 1.0 | 79.16 ± 0.4 |
| | $E_5$ | CMKG - 2.5% | 39.14 ± 0.1 | 40.37 ± 0.4 | 43.92 ± 1.1 | 45.21 ± 1.2 |
| | $E_6$ | CMKG - 5% | 44.05 ± 0.2 | 45.18 ± 1.0 | 54.12 ± 1.3 | 55.10 ± 1.1 |
| | $E_7$ | CMKG - 7.5% | 58.64 ± 0.2 | 60.13 ± 1.1 | 70.64 ± 0.7 | 72.17 ± 1.1 |
| | $E_8$ | CMKG - 10% | 77.51 ± 1.0 | 79.15 ± 0.3 | 82.37 ± 0.6 | 83.23 ± 0.5 |
| Marketed formulations | Hypromellose | HPMC - 0.3% | 42.59 ± 1.1 | 46.17 ± 1.5 | 47.30 ± 0.6 | 52.15 ± 0.3 |
| | Refresh tears | NaCMC - 0.5% | 44.86 ± 0.4 | 49.69 ± 1.2 | 51.69 ± 0.2 | 55.47 ± 0.6 |

When changing the dispensing angle from 90° to 45°, the mean drop weight of the marketed formulation, NaCMC (0.5% w/v) and HPMC (0.3% w/v) eye lubricant solution decreased by about 10% (P<0.001). However, no significant differences were observed for formulations containing carbamoylethyl katira/carboxymethyl katira.

Overall, the pharmaceutical and patient determinants of eye drops size suggested eye drop formulations $E_1$ (carbamoylethyl katira 2.5% w/v), $E_2$ (carbamoylethyl katira 5% w/v), $E_5$ (carboxymethyl katira 2.5% w/v) and $E_6$ (carboxymethyl katira 5% w/v) could be selected for further study.

The in vitro antimicrobial activity of $E_1$ (carbamoylethyl katira 2.5% w/v), $E_2$ (carbamoylethyl katira 5% w/v), $E_5$ (carboxymethyl katira 2.5% w/v) and $E_6$ (carboxymethyl katira 5% w/v) eye drop formulations was examined against *Staphylococcus aureus* by agar well diffusion method. The results of zone of inhibitions are shown in Table 12. The findings pointed towards maximum activity of $E_2$ eye drop formulation. The zone of inhibition different eye drop formulations follows the order $E_2 > E_6 > E_1 > E_5$. Thus, $E_2$ and $E_6$ were selected for further study.

TABLE 12

Results of In-vitro antimicrobial activity of eye lubricant solution

| Eye lubricant formulation code | Concentration of eye lubricant (w/v) | Zone of inhibition (mm) |
|---|---|---|
| $E_1$ | CEKG - 2.5% | 11 ± 0.2 |
| $E_2$ | CEKG - 5% | 15 ± 0.2 |
| $E_5$ | CMKG - 2.5% | 9 ± 0.3 |
| $E_6$ | CMKG - 5% | 12 ± 0.1 |

Example-14: Sterility Testing

A sterility test may be defined as 'a test that critically assesses whether a sterilized pharmaceutical product is free from contaminating microorganisms' as per Indian Pharmacopoeia (2007), the sterility testing of eye drop formulations was carried out using Method B (direct inoculation method) in Nutrient Broth (NB), Fluid Thioglycollate Medium (FTG), Soyabean Casein Digest Medium (SCD). To evaluate sterility of eye drop formulations, 5 ml of eye drop formulation was withdrawn from the test container with a sterile syringe aseptically and transferred to a 5 ml of the culture medium. Incubated the 'inoculated media' for not less than 14 days at: 30-35° C. for 'Fluid Thioglycollate Medium', 20-25° C. for 'Soyabean-Casein Digest Medium' and 37° C. for Nutrient Broth Media and observed for growth of microorganisms. Sterility testing of all the eye drop formulations was conducted as per Indian Pharmacopoeia, (2010) employing dilution method. The carbamoylethyl katira/carboxymethyl katira eye drop formulations showed antibacterial property. The antimicrobial testing suggested 1% w/v concentration of both carbamoylethyl katira/carboxymethyl katira was ineffective for antibacterial activity. Therefore, all the eye drop formulations were diluted with sterile water for injection so as to reach less than 1% w/v concentration of carbamoylethyl katira/carboxymethyl katira. and sterility test was conducted in FTG, SCD and NB media.

The results of sterility testing indicated all the eye drop batches pass test according to the Indian Pharmacopoeia, 2007. The results suggested eye drop formulations are free from any viable microorganisms and does not promote growth of any microbial growth

Example-15: Stability Studies

The sterile formulations ($E_2$ and $E_6$) were subjected to formulation stability studies and microbial stability studies. For the formulation stability studies the sterile formulations were subjected to stability studies at temperature 30° C./65% RH in stability chamber for two month according to ICH guidelines. Formulations were evaluated for appearance, presence of any visible particulate matter, pH, viscosity, specific gravity, surface tension periodically and FTIR-ATR analysis (for any possibility of degradation).

For the microbial stability studies, two drops of eye drop formulation was withdrawn from the container after opening the bottle cover and exposure to non sterile area for 15 min. these two drops were put on a sterilized agar petriplates under aseptic conditions and incubated for 24 hr for any possibility of growth. This procedure was repeated three times in a day for 30 days.

The results of formulation stability study in Table 13 suggest the compatibility of formulation ingredients and thus can offer satisfactory shelf life of preparation. There is no significant difference in considerable parameters over the study period. The FTIR-ATR spectra suggested absence of degradation of carbamoylethyl katira/carboxymethyl katira. eye drop formulations.

The results of microbial stability studies suggested absence of microbes when exposed to non sterile area three times a day for 30 days. This indicated the prepared eye drops did require any preservative that generally causes dry eye infections over prolonged use.

TABLE 13

Results of formulation stability study

Storage period (days) at 30° C./65% RH

| | $E_2$ | | | | $E_6$ | | | |
|---|---|---|---|---|---|---|---|---|
| Parameters | 15 | 30 | 45 | 60 | 15 | 30 | 45 | 60 |
| Appearance | Clear | Clear | Clear | Clear | Clear | Clear | Clear | Clear |
| pH | 7.4 ± 0.3 | 7.4 ± 0.3 | 7.3 ± 0.4 | 7.3 ± 0.3 | 7.4 ± 0.2 | 7.3 ± 0.4 | 7.2 ± 0.3 | 7.2 ± 0.1 |
| Specific gravity (g/cm³) | 1.016 ± 0.3 | 1.016 ± 0.2 | 1.015 ± 0.3 | 1.015 ± 0.1 | 1.013 ± 0.5 | 1.012 ± 0.3 | 1.010 ± 0.4 | 1.010 ± 0.2 |
| Viscosity (cP) | 6.50 ± 0.4 | 6.50 ± 0.5 | 6.43 ± 0.2 | 6.41 ± 0.3 | 5.93 ± 0.2 | 5.90 ± 0.2 | 5.90 ± 0.3 | 5.85 ± 0.1 |
| Surface tension (dyne/cm) | 42.7 ± 0.2 | 42.7 ± 0.4 | 42.3 ± 0.2 | 42.1 ± 0.3 | 45.3 ± 0.3 | 45.2 ± 0.4 | 45.2 ± 0.2 | 44.8 ± 0.3 |

Example-16: Ex-Vivo Ocular Tolerance Studies

Draize Rabbit Eye Test

The protocol of the study was approved by Institutional Animal Ethical Committee as per number 107/99/CPCSEA/2013-43. Draize Eye Irritation Test as per OECD guideline No 405(2) was performed on rabbits to evaluate the irritation potential of the eye drop formulations. Albino rabbits of either sex were used. The animals were maintained on standard animal feed and had free access to water. The animals were kept under standard conditions. The test was based on determining the presence of ocular pathophysiological changes like corneal opacity, congestion, swelling of iris, haemorrhage, destruction of iris, chemosis, reddening of conjunctiva (hyperemia), discharge of mucus leading to moistening of eyelids and hair etc. For the evaluation of the eye drop formulation, 0.1 ml of eye drop formulation was instilled into the conjunctival cul-de-sac of rabbit eye. The eyes were observed at durations of 0, 12, 24, 48 and 72 hours for any of the above pathophysiological changes.

Hen's Egg Test—Chorioallantoic Membrane Test (HET-CAM) Method

The ocular tolerance of prepared eye drop formulations was evaluated employing the hen's egg test on chorioallantoic membrane of chicken eggs (HET-CAM test). HET CAM study is established alternative technique to Draize rabbit eye test to check potential irritation effects in the eye. This study estimates the irritation effects such as haemorrhage, lysis and coagulation in the eye caused within 5 min after applying the formulation on chorioallantoic membrane (CAM) of chicken eggs. For this study white leghorn eggs aged 7 days weighing 60.0+5.0 g were used and these eggs were purchased from Haryana Breeding farm and hatchery (Vill. ker kheri, Jind, Haryana). The selected eggs were incubated for 10 days. Large end upwards, in a rotating tray at 37.0±0.5° C. and 62.5±1.5% relative humidity. On day 9 the eggs were placed in the lower part of the incubator and incubation was continued without rotation. On day 10 the eggs were candled with a laser source lamp to ensure their viability. Non-fertilized or non-viable eggs were rejected. The airspace delimited by the inner membrane at the large end of the egg was marked after which the eggshell was removed. The inner membrane, directly in contact with the CAM, was moistened with 0.9% NaCl solution and the egg was returned to a temperature of 37° C. for a maximum of 20 min. After incubation, the NaCl solution was gently removed and the inner membrane was removed by means of curved-end forceps without injuring any underlying blood vessels. The CAM then became visible and was carefully examined to confirm its integrity. Finally, the CAM was treated with an aliquot of 0.5 ml of eye drop formulations, 10% benzalkonium chloride (as a positive chloride) and saline (as a negative control). The CAM was observed for appearance of irritation effect such as haemorrhage, lysis and coagulation for 5 min and scored. Time values obtained after the observation of each reaction were combined into an in vitro eyeirritation score (IS) generated by means of the following equation (Yadav, S., Ahuja, M., Kumar, A., & Kaur, H. (2014). Gellan-thioglycolic acid conjugate: Synthesis, characterization and evaluation as mucoadhesive polymer. Carbohydrate polymers, 99, 601-607):

$$IS = \frac{(301 - secH) \times 5}{300} + \frac{(301 - secL) \times 7}{300} + \frac{(301 - secC) \times 9}{300}$$

where secH=reaction time in seconds for haemorrhage, secL=reaction time in seconds for lysis, secC=reaction time in seconds for intra or extravascular coagulation if no reaction have been occurred during 5 min then set secH, secL, secC=301

The results obtained during Draize rabbit eye test are summarized in Table 14. No pathophysiological changes were observed after 1 hr, 4 hr, 24 hr, 48 hr and 72 hr of topical instillation of eye drop formulations $E_2$ (carbamoylethyl katira 5% w/v) and $E_6$ (carboxymethyl katira 5% w/v) indicating the formulations are safe for ocular use.

HET-CAM test showed maximum irritation score for benzalkonium chloride (10% w/v) solution. Since, it is severe irritant that give haemorrhage, coagulation in (secC=52) However, irritation score for eye drop formulations $E_2$ (carbamoylethyl katira 5% w/v) and $E_6$ (carboxymethyl katira 5% w/v) was found to be zero indicated for non irritant. This suggested carbamoylethyl katira/carboxymethyl katira formulations were safe, non irritant and non-toxic.

Example-17: Eye Lubrication Potential

Rabbit Dry Eye Model Development and Tear Production Measurement

This study was conducted as per model proposed by (Xiong, C., Chen, D., Liu, J., Liu, B., Li, N., Zhou, Y., & Wang, Z. (2008). A rabbit dry eye model induced by topical medication of a preservative benzalkonium chloride. Investigative ophthalmology & visual science, 49(5), 1850-1856). To study the eye lubrication evaluation of formulations, rabbits were used. The rabbits were induced with dry eye by administration of 2 drops of 0.2% Benzalkonium chloride (BAC) solution twice a day for three days. Three days of topical instillation was found to be suitable for inducing the inflammatory symptoms and decreasing the tear production to produce moderate dry eye without causing permanent damage to the rabbit eye. The dry eye animal model produced by above procedure resembled the evaporative dry eye state in humans.

Schirmer I tear test was used to measure tear production from the rabbit eyes (both healthy and dry eye state). The test comprised of placing a small strip of Whatmann 41 filter paper cut to dimensions; 35×5 mm after sterilisation inside the lower conjunctival sac after making a notch of 5 mm from one end of the strip. The eyes were closed for 5 minutes. The 30 mm segment was left to hang over the lower lid. After 5 minutes, the strip was removed and the wetted length was measured. No anaesthetic was used as topical anaesthesia tends to decrease the test values and affects the reproducibility of the Schirmer tear test. The dry eye induction was confirmed by decrease in tear production values and by the presence of the dry eye symptoms as observed by digital camera. The inflammatory symptoms produced were photographed.

Treatment with Prepared Eye Drop Formulations in Rabbit Dry Eye Model

Subsequent to three days of topical instillation of 0.2% BAC in rabbits, the treatment of the rabbits was started. The formulation was instilled twice a day. Post-instillation of the formulation, the gradual changes in the various components of inflammatory symptoms like reddening of the conjunctiva (bulbar and tarsal) and iris, conjunctival hyperemia, mucosal discharge from the eye, wetting of eyelids, hairs and surrounding regions of the eye, tearing and the ease of opening of eyes of rabbits were photographed and the increase in tear production values was measured. The treatment was continued till the treated eye was normalised to a healthy state with complete absence of inflammatory symptoms and the tear readings normalised to basal values (i.e. pertaining to healthy eye) Xiong, C., Chen, D., Liu, J., Liu, B., Li, N., Zhou, Y., . . . & Wang, Z. (2008). A rabbit dry eye model induced by topical medication of a preservative benzalkonium chloride. Investigative ophthalmology & visual science, 49(5), 1850-1856).

Figure 6:
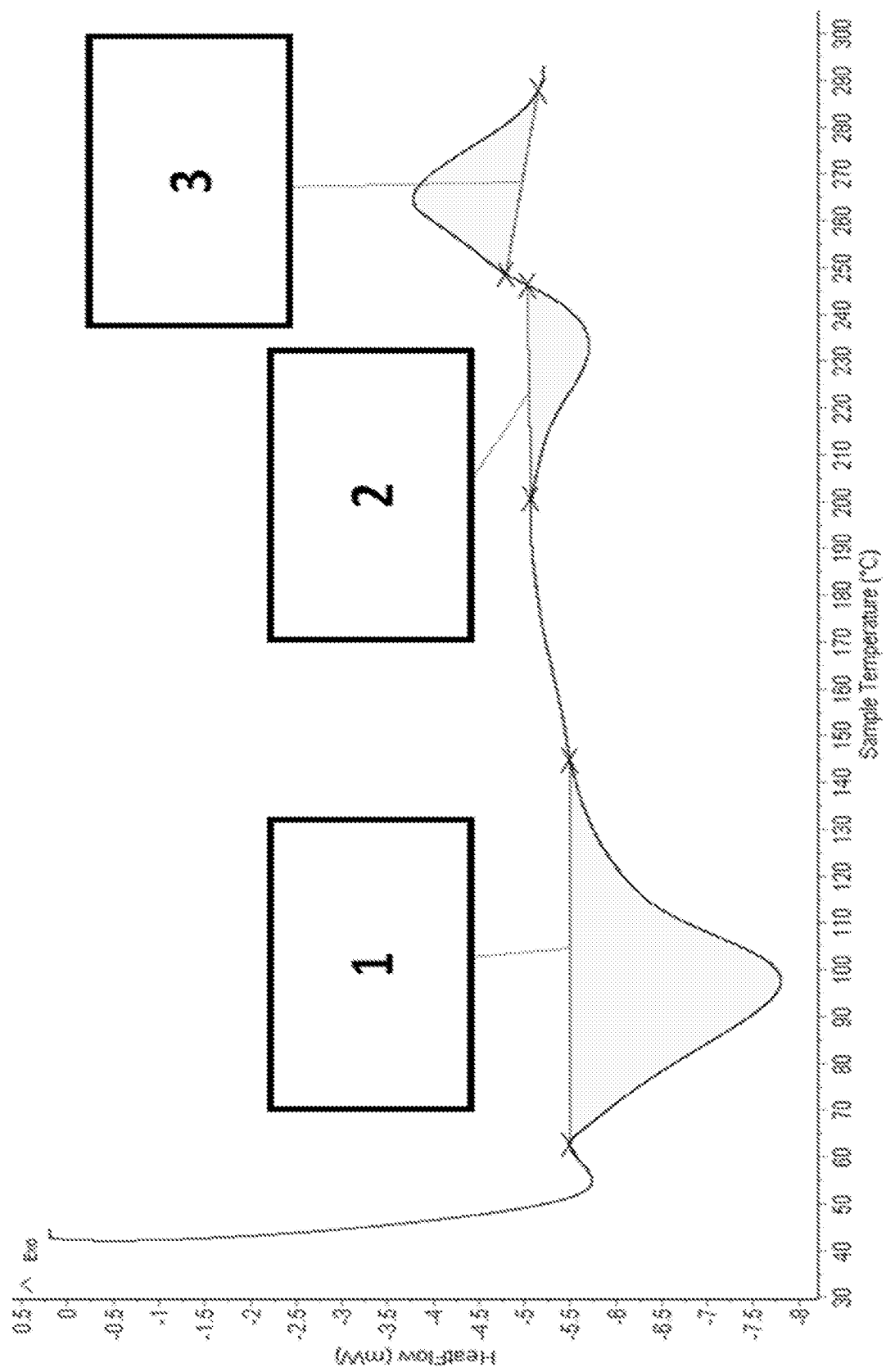
FIG. 6 illustrates measurement of tear secretion in rabbit eyes employing Schirmer test. Data box 1—Heat: 161.262 J/g; T: 62.81 and 144.80 ° C.; t: 200.2 and 676.2 s; Peak Maximum: 97.644 ° C. / 396.8 s; Peak Height: -2.304 mW; Onset 66.412 ° C. / 219.286 s; Offset 120.159 ° C. / 529.83 s; Baseline Type: Linear. Data box 2 - Heat: 32.461 J/g; T: 200.63 and 246.26 ° C.; t: 1,008.0 and 1,280.4 s; Peak Maximum: 233.63 ° C. / 1,205 s; Peak Height: -0.662 mW; Onset 211.265 ° C. / 1,071.403 s; Offset 246.262 ° C. / 1,280.391 s; Baseline Type: Linear. Data box 3—Heat: -49.802 J/g; T: 248.62 and 287.73 ° C.; t: 1,294.4 and 1,527.8 s; Peak Maximum: 265.033 ° C. / 1,392 s; Peak Height: 1.163 mW; Onset ! / !; Offset 284.102 ° C. / 1,506.258 s; Baseline Type: Linear.

Potential of eye drop formulations $E_1$ (carbamoylethyl katira 2.5% w/v), $E_2$ (carbamoylethyl katira 5% w/v), $E_5$ (carboxymethyl katira 2.5% w/v) and $E_6$ (carboxymethyl katira 5% w/v) for the treatment of dry eye disease was further evaluated using dry eye model induced by 0.2% benzalkonium chloride ( ) Xiong, C., Chen, D., Liu, J., Liu, B., Li, N., Zhou, Y., . . . & Wang, Z. (2008). A rabbit dry eye model induced by topical medication of a preservative benzalkonium chloride. Investigative ophthalmology & visual science, 49(5), 1850-1856).). Schirmer test was employed to quantitate tear production. The strip (35×5 mm) was to measure amount of tear produced. The schirmer test score (reported as mm of wet strip after 3 min of insertion)

obtained before and after the treatment with $E_1$ (carbamoylethyl katira 2.5% w/v), $E_2$ (carbamoylethyl katira 5% w/v), $E_5$ (carboxymethyl katira 2.5% w/v) and $E_6$ (carboxymethyl katira 5% w/v) eye drop formulations are shown in Table 15 and images taken at each time point of measurement are shown in Table 16. It was observed that administration of rabbit eyes with BAC (0.2% w/v) produce dry eye symptoms like ocular inflammation, mucosal discharge and swelling of eye lids and significantly reduced the tear production within 2 days (FIG. 6). The treatment of dry eyes with eye drop formulations $E_1$ (carbamoylethyl katira 2.5% w/v), $E_2$ (carbamoylethyl katira 5% w/v), $E_5$ (carboxymethyl katira 2.5% w/v) $E_6$ (carboxymethyl katira 5% w/v) or marketed formulations (Hypromellose or Refresh tears) enhanced tear production. The $E_2$ (carbamoylethyl katira 5% w/v) and $E_6$ (carboxymethyl katira 5% w/v) eye drop formulations showed prompt healing (within 3 days postinfection) from dry eye disease as compare to marketed formulations. However, the $E_1$ (carbamoylethyl katira 2.5% w/v) or $E_5$ (carboxymethyl katira 2.5% w/v) eye drop formulations show no significant difference in tear enhancement when compare with marketed formulations. Interestingly, all the formulations with $E_1$ (carbamoylethyl katira 2.5% w/v), $E_2$ (carbamoylethyl katira 5% w/v), $E_5$ (carboxymethyl katira 2.5% w/v), $E_6$ (carboxymethyl katira 5% w/v) and marketed formulations raised the tear production to normal after 5 days (postinfection) suggesting eye lubricating potential of carbamoylethyl katira (2.5% w/v-5% w/v) and carboxymethyl katira (2.5% w/v-5% w/v). Overall, eye drop formulations $E_2$ (carbamoylethyl katira 5% w/v) and $E_6$ (carboxymethyl katira 5% w/v) could be used as the best eye drop formulations for the treatment of dry eyes.

We claim:
1. A sterile lubricant formulation comprising:
    carbamoylethyl katira, prepared from a katira gum, in the range of 2.5% w/v to 10% w/v;
    sterile water; and
    additives,
    wherein said formulation shows antibacterial activity.
2. The sterile lubricant formulation as claimed in claim 1, wherein the katira gum is obtained from *Cochlospermum religiosum*.
3. The sterile lubricant formulation as claimed in claim 1, wherein the additives are selected from the group consisting of sodium chloride, a surfactant, another agent as an emulsifier, and combinations thereof, in a water based emulsion.
4. The sterile lubricant formulation as claimed in claim 1, wherein said formulation shows antibacterial activity against *Staphylococcus aureus*.
5. The sterile lubricant formulation as claimed in claim 1, wherein said formulation is suitable for use in treatment of dry eye disease.
6. A process for the preparation of the sterile lubricant formulation of claim 1, wherein said process comprises of the following steps:
    a) soaking a katira gum in water for a time period of 14 to 20 hrs to obtain a homogenized gel;
    b) stirring the homogenized gel obtained in step (a) for 30 to 45 minutes followed by addition of 25 ml of a 28% w/v to 44% w/v ice cold sodium hydroxide solution with stirring and additional stirring for 30 min after the addition of the ice cold sodium hydroxide solution to obtain a basic reaction mixture;
    c) adding 11% w/v to 18% w/v of acrylamide to the basic reaction mixture obtained in step (b) with constant stirring for 1 hr to obtain a reaction mixture;
    d) irradiating the reaction mixture obtained in step (c) in a microwave reactor at 450 watt for a time period of 0.5 to 1 min followed by a cooling cycle for a time period of 1 to 2 min at a temperature of 4° C. to 10° C. in ice bath;

TABLE 15

Results of schirmer test for lacrimal secretion

| Rabbit eye condition | Time (days) | Control (untreated) | Eye lubricant formulations | | | | Marketed fromulations | |
|---|---|---|---|---|---|---|---|---|
| | | | $E_1$ | $E_2$ | $E_5$ | $E_6$ | Refresh tears (NaCMC) | Hypromellose (HPMC) |
| | | Tear secretion level (mm) raised in a strip (35 × 5 mm) | | | | | | |
| Normal | 0 | 15 ± 0.5 | 15 ± 0.3 | 15 ± 0.2 | 14 ± 0.7 | 14 ± 0.3 | 13 ± 0.6 | 12 ± 0.4 |
| Administration of 0.2% w/v BAC solution to induce dry eyes (2 drops twice a day) | | | | | | | | |
| Dry eye disease induction phase | 1 | 14 ± 0.4 | 12 ± 0.6 | 14 ± 0.4 | 12 ± 0.6 | 9 ± 0.4 | 10 ± 0.3 | 10 ± 0.7 |
| | 2 | 12 ± 0.4 | 11 ± 0.4 | 12 ± 0.7 | 10 ± 0.5 | 8 ± 0.2 | 8 ± 0.3 | 8 ± 0.4 |
| | 3 | 9 ± 0.6 | 8 ± 0.5 | 8 ± 0.3 | 7 ± 0.4 | 8 ± 0.4 | 7 ± 0.5 | 8 ± 0.2 |
| Administration of prepared and marketed eye lubricant formulations (2 drops twice a day) | | | | | | | | |
| Treatment phase | 4 | 7 ± 0.7 | 9 ± 0.7 | 10 ± 0.6 | 7 ± 0.2 | 10 ± 0.5 | 7 ± 0.4 | 10 ± 0.3 |
| | 5 | 6 ± 0.3 | 10 ± 0.4 | 12 ± 0.4 | 9 ± 0.4 | 11 ± 0.6 | 10 ± 0.7 | 10 ± 0.5 |
| | 6 | 5 ± 0.2 | 12 ± 0.2 | 15 ± 0.3 | 12 ± 0.3 | 14 ± 0.7 | 10 ± 0.4 | 11 ± 0.3 |
| | 7 | 5 ± 0.3 | 15 ± 0.4 | 15 ± 0.2 | 14 ± 0.5 | 15 ± 0.4 | 12 ± 0.3 | 12 ± 0.1 |
| | 8 | 5 ± 0.5 | 15 ± 0.3 | 15 ± 0.2 | 14 ± 0.2 | 15 ± 0.3 | 13 ± 0.5 | 13 ± 0.4 |

NaCMC = Sodium carboxymethyl cellulose,
HPMC = Hydroxypropyl methyl cellulose,
BAC = Benzalkonium chloride e) repeating the step (d) for 3 to 7 times followed by neutralization with dilute glacial acetic acid to obtain a neutralized reaction mixture;

f) precipitating the neutralized reaction mixture obtained in step (e) with solvents followed by washing with a precipitating solvent to obtain a precipitate of carbamoylethyl katira;

g) filtering and drying the precipitate of carbamoylethyl katira obtained in step (f) to obtain a dried carbamoylethyl katira;

h) dissolving 2.5% to 10% w/v of dried carbamoylethyl katira obtained in step (g) in luke warm sterile water followed by filtration through a 0.22 μm filtration system to form a lubrication formulation of carbamoylethyl katira, filled in a sterilized vial and sealed; and i) sterilizing the lubricant formulation of carbamoylethyl katira obtained in step (h) at a temperature in the range of 118° C. to 121° C. for a time period of 20 to 40 minutes to obtain said sterilized lubricant formulation of claim 1.

7. The process as claimed in claim 6, wherein the ratio of glacial acetic acid and water as diluent in step (e) is 1:1 for neutralization of reaction.

8. The process as claimed in claim 6, wherein drying of carbamoylethyl katira in step (g) is carried out using lyophilization at a temperature in the range of −80° C. for a time period of 72 to 96 hours, or oven drying at a temperature of 45 to 55° C. for a time period of 3.5 to 4.5 days or 60° C. for a time period of 1.5 to 2.5 days to obtain the dried carbamoylethyl katira.

9. The process as claimed in claim 6, wherein the sterilizing in step (i) comprises autoclaving at temperature in the range of 118-121° C. and a pressure of 15 psi to obtain sterilized lubricant formulation.

10. The sterile lubricant formulation as claimed in claim 1, wherein said formulation is in the form of a drop, the drop being formed by dropper bottle having a dropper Tip A with an orifice diameter of 0.45 mm or a dropper Tip B with an orifice diameter of 0.70 mm.

11. The sterile lubricant formulation as claimed in claim 10, wherein a weight of the drop is in the range of 35.4-81 mg and a volume of the drop is in the range of 35-79 μL being formed by the dropper Tip A.

12. The sterile lubricant formulation as claimed in claim 10, wherein a weight of the drop is in the range of 42-85 mg and a volume of the drop is in the range of 42-83 μL being formed by the dropper Tip B.

13. The sterile lubricant formulation of claim 1, wherein the formulation is a non-irritant with a zero irritation score.

14. A sterile ocular solution comprising carbamoylethyl katira prepared from a katira gum, in the range of 2.5% to 10% w/v, sterile water and a pH adjusting agent;

wherein said sterile ocular solution shows antibacterial activity.

\* \* \* \* \*